United States Patent [19]

Kogan et al.

[11] Patent Number: 5,919,768
[45] Date of Patent: Jul. 6, 1999

[54] DI- AND TRIVALENT SMALL MOLECULE SELECTIN INHIBITORS

[75] Inventors: Timothy P. Kogan, Sugarland; Brian Dupre; Ian L. Scott, both of Houston; Huong Bui, Pearland; Kathy L. Wheeler, Wichita Falls; Karin M. Keller; Jamal M. Kassir, both of Houston, all of Tex.

[73] Assignee: Texas Biotechnology Corporation, Houston, Tex.

[21] Appl. No.: 08/981,580

[22] PCT Filed: Jun. 26, 1996

[86] PCT No.: PCT/US96/11032

§ 371 Date: Feb. 11, 1998

§ 102(e) Date: Feb. 11, 1998

[87] PCT Pub. No.: WO97/01335

PCT Pub. Date: Jan. 16, 1997

[51] Int. Cl.⁶ .......... A61K 31/35; A61K 31/70; C07D 309/10; C07H 15/00

[52] U.S. Cl. .......... 514/25; 514/316; 514/460; 536/4.1; 536/18.2; 546/187; 549/415

[58] Field of Search .......... 514/25, 316, 460; 536/4.1, 18.2; 546/187; 549/415

[56] References Cited

U.S. PATENT DOCUMENTS 5,444,050  8/1995  Kogan et al. .......... 514/25
5,498,775  3/1996  Novak et al. .......... 514/25

*Primary Examiner*—Deborah C. Lambkin
*Attorney, Agent, or Firm*—Rockey, Milnamow & Katz

[57] ABSTRACT

The present invention provides compounds having structure (II), and the pharmaceutically acceptable salts, esters, amides and prodrugs thereof.

9 Claims, No Drawings

DI- AND TRIVALENT SMALL MOLECULE SELECTIN INHIBITORS

This application is a 371 of PCT/US 96/11032 filed Jun. 26, 1996.

TECHNICAL FIELD

This invention relates to compounds that inhibit the binding of E-selectin, P-selectin or L-selectin to sialyl-Lewis$^x$ and sialyl-Lewis$^a$ and to methods of inhibiting the binding of E-selectin, P-selectin or L-selectin to sialyl-Lewis$^x$ or sialyl-Lewis$^a$ using said compounds. This invention also relates to pharmaceutically active compositions comprising compounds that inhibit the binding of E, P or L-selectin to sialyl-Lewis$^x$ or sialyl-Lewis$^a$.

BACKGROUND OF THE INVENTION

E-selectin, which has also been called ELAM-1 for endothelial leukocyte adhesion molecule-1 and LECAM-2 for lectin cell adhesion molecule, is a glycoprotein that is found on the surface of endothelial cells, the cells that line the interior wall of capillaries. E-selectin recognizes and binds to the carbohydrate sialyl-Lewis$^x$ (sLe$^x$), which is present on the surface of certain white blood cells. E-selectin helps white blood cells recognize and adhere to the capillary wall in areas where the tissue surrounding the capillary has been infected or damaged. E-selectin is actually one of three selectins now known. The other two are L-selectin and P-selectin. P-selectin is expressed on inflamed endothelium and platelets, and has much structural similarity to E-selectin and can also recognize sialyl-Lewis$^x$. L-selectin is expressed on leukocytes and also has much structure similarity to P- and E-selectins. The structure of sialyl-Lewis$^x$ and sialyl-Lewis$^a$ (sLe$^a$) are shown in formulas I$_a$ and I$_b$ below:

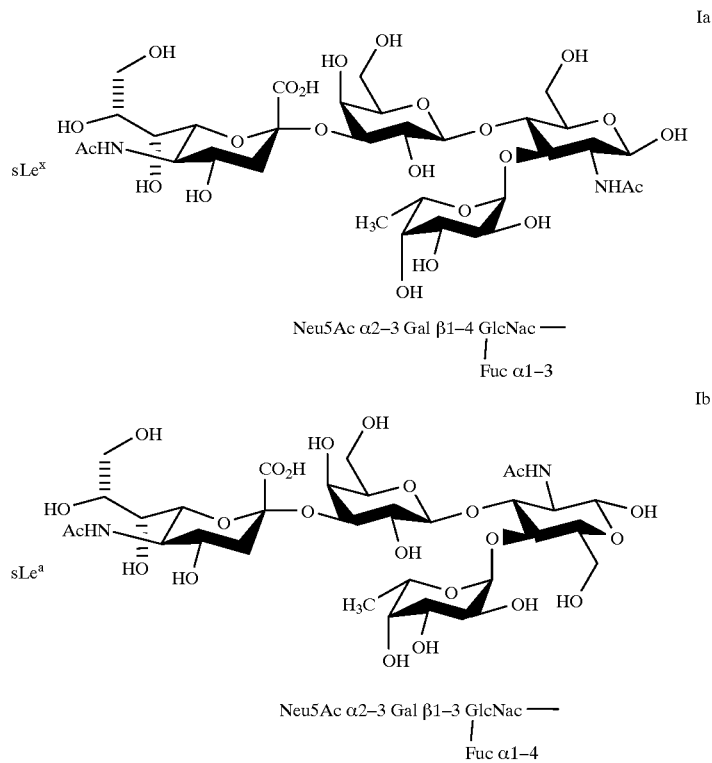

When a tissue has been invaded by a microorganism or has been damaged, white blood cells, also called leukocytes, play a major role in the inflammatory response. One of the most important aspects of the inflammatory response involves the cell adhesion event. Generally, white blood cells are found circulating through the bloodstream. However, when a tissue is infected or becomes damaged, the white blood cells must be able to recognize the invaded or damaged tissue and be able to bind to the wall of the capillary near the affected tissue and diffuse through the capillary into the affected tissue. E-selectin helps two particular types of white blood cells recognize the affected sites and bind to the capillary wall so that these white blood cells may diffuse into the affected tissue.

There are three main types of white blood cells: granulocytes, monocytes and lymphocytes. Of these categories, E-selectin recognizes sLe$^x$ presented as a glycoprotein or glycolipid on the surface of monocytes and neutrophils. Neutrophils are a subclass of granulocytes that phagocytose and destroy small organisms, especially bacteria. Monocytes, after leaving the bloodstream through the wall of a capillary, mature into macrophages that phagocytose and digest invading microorganisms, foreign bodies and senescent cells.

Monocytes and neutrophils are able to recognize the site where tissue has been damaged by binding to E-selectin, which is produced on the surface of the endothelial cells lining capillaries when the tissue surrounding a capillary has been infected or damaged. Typically, the production of E-selectin and P-selectin is increased when the tissue adjacent to a capillary is affected. P-selectin is present constitutively in storage granules from which it can be rapidly mobilized to the cell surface after the endothelium has been activated. In contrast, E-selectin requires de novo RNA and protein synthesis, and peak expression is reached about 4–6 hours after activation, and declines to basal levels after about 24–48 hours. White blood cells recognize affected areas because sLe$^x$ moieties present on the surface of the white blood cells bind to E-selectin and P-selectin. This binding slows the velocity of white blood cells circulating through the bloodstream, since it mediates the rolling of leukocytes along the activated endothelium prior to integrin-mediated attachment and migration, and helps to localize white blood cells in areas of injury or infection.

While white blood cell migration to the site of injury helps fight infection and destroy foreign material, an accumulation of an excessive number of white blood cells can cause widespread tissue damage. Compounds capable of blocking this process, therefore, may be beneficial as therapeutic agents. Thus, it would be usefill to develop inhibitors that would prevent the binding of white blood cells to E-selectin or P-selectin. For example, some of the diseases that might be treated by the inhibition of selectin binding to sLe$^x$ include, but are not limited to, ARDS, Crohn's disease, septic shock, traumatic shock, multi-organ failure, autoimmune diseases, asthma, inflammatory bowel disease, psoriasis, rheumatoid arthritis and reperfusion injury that occurs following heart attacks, strokes and organ transplants. In addition to being found on some white blood cells, sLe$^a$, a closely related regiochemical isomer of sLe$^x$, is found on various cancer cells, including lung and colon cancer cells. It has been suggested that cell adhesion involving sLe$^a$ may be involved in the metastasis of certain cancers.

SUMMARY OF THE INVENTION

The present invention provides compounds having the structure of formula II below:

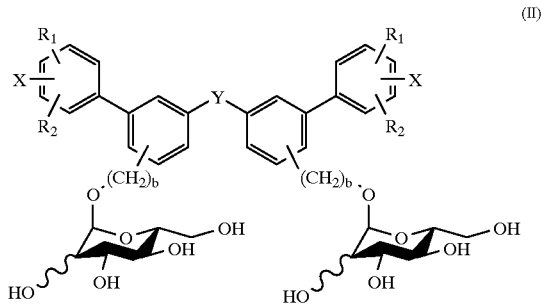

(II)

wherein X is selected from the group consisting of —CN, —(CH$_2$)$_n$CO$_2$H, —(CH$_2$)$_n$CONHOH, —O(CH$_2$)$_m$CO$_2$H, —O(CH$_2$)$_m$CONHOH, —(CH$_2$)$_n$CONHNH$_2$, —(CH$_2$)$_n$COZ, —(CH$_2$)$_n$Z, —CH(CO$_2$H)(CH$_2$)$_m$CO$_2$H, —(CH$_2$)$_n$O(CH$_2$)$_m$CO$_2$H, —CONH(CH$_2$)$_m$CO$_2$H, —CH(OZ)(CO$_2$H), —CH(Z)(CO$_2$H), —(CH$_2$)$_n$SO$_3$H, —(CH$_2$)$_n$PO$_3$D$_1$D$_2$, —NH(CH$_2$)$_m$CO$_2$H, —CONH(CHR$_3$)CO$_2$H, (1-H-tetrazolyl-5-alkyl-), and —OH;

For divalent structures, Y is —(CH$_2$)$_f$—, —CO(CH$_2$)$_f$CO—, —(CH$_2$)$_f$O(CH$_2$)$_f$—, —CO(CH$_2$)$_f$O(CH$_2$)$_f$CO—, —(CH$_2$)$_g$S(O)$_b$(CH$_2$)$_f$S(O)$_b$(CH$_2$)$_g$—, —CO(CH$_2$)$_g$S(O)$_b$(CH$_2$)$_f$S(O)$_b$(CH$_2$)$_g$CO—, —(CH$_2$)$_f$V(CH$_2$)$_f$—, —(CH$_2$)$_f$COVCO(CH$_2$)$_f$—, —CO(CH$_2$)$_f$OVCO(CH$_2$)$_f$CO—, —CO(CH$_2$)$_f$V(CH$_2$)$_f$CO—, —CONH(CH$_2$)$_f$NHCO—, —CO(CH$_2$)$_f$W(CH$_2$)$_f$CO—, —(CH$_2$)$_f$WSW(CH$_2$)$_f$—, —(CH$_2$)$_f$CONH(CH$_2$)$_f$NHCO(CH$_2$)$_f$—, —(CH$_2$)$_f$COW(CH$_2$)$_f$WCO(CH$_2$)$_f$—, or —CH$_2$(CH$_2$)$_f$W(CH$_2$)$_f$CH$_2$— where V is —N[(CH$_2$)$_q$]$_2$N— and q is independently 2 to 4, and W is aryl or heteroaryl;

For trivalent structures, Y is:

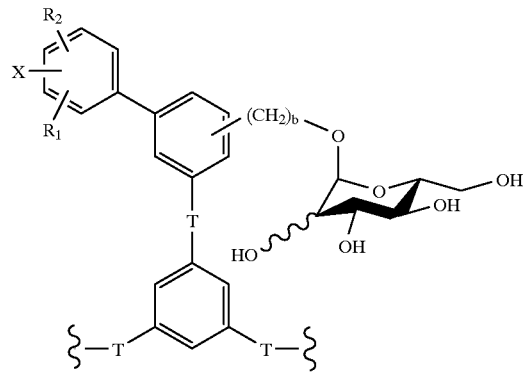

and T is selected from the group consisting of —(CH$_2$)$_f$—, —CO(CH$_2$)$_f$—, —(CH$_2$)$_g$S(O)$_b$(CH$_2$)$_f$—, and —CO(CH$_2$)$_g$S(O)$_b$(CH$_2$)$_f$—, where the carbonyl group is positioned contiguous to the biphenyl unit;

R$_1$ and R$_2$ are independently selected from the group consisting of hydrogen, alkyl, halogen, —OZ, —NO$_2$, —(CH$_2$)$_n$CO$_2$H, —NH$_2$ and —NHZ;

R$_3$ is selected from the group consisting of hydrogen, alkyl, aralkyl, hydroxyalkyl, aminoalkyl, alkyl carboxylic acid and alkyl carboxamide;

f is 1 to 16, g is 0 to 6, n is 0 to 6, m is 1 to 6, p is 0 to 6, b is 0 to 2, Z is alkyl, aryl or aralkyl, and D$_1$ and D$_2$ are independently hydrogen or alkyl, and the pharmaceutically acceptable salts, esters, amides and prodrugs thereof.

More particularly, this invention provides compounds of the formula III;

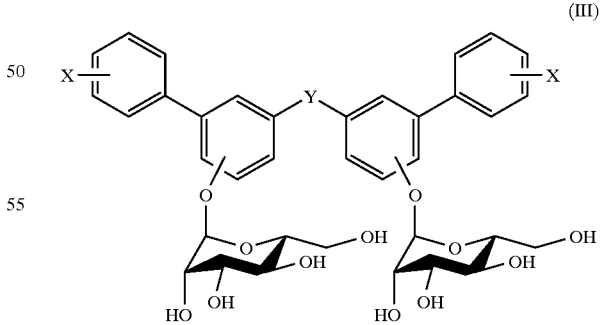

(III)

where X is —COOH, —(CH$_2$)$_n$COOH or —O(CH$_2$)$_n$COOH and Y is —(CH$_2$)$_n$—, —(CH$_2$)$_n$W(CH$_2$)$_n$—, —(CH$_2$)$_n$WOW(CH$_2$)$_n$—, —(CH$_2$)$_n$S(CH$_2$)$_n$S(CH$_2$)$_n$—, —CO(CH$_2$)$_n$CO—, or —(CH$_2$)$_n$COW(CH$_2$)$_n$WCO(CH$_2$)$_n$— where W and n are as defined above.

Particularly preferred compounds include:

A
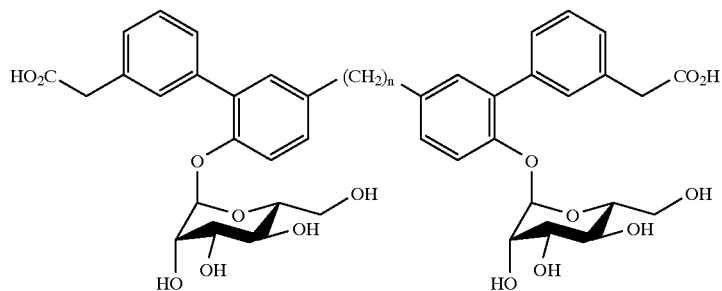
B
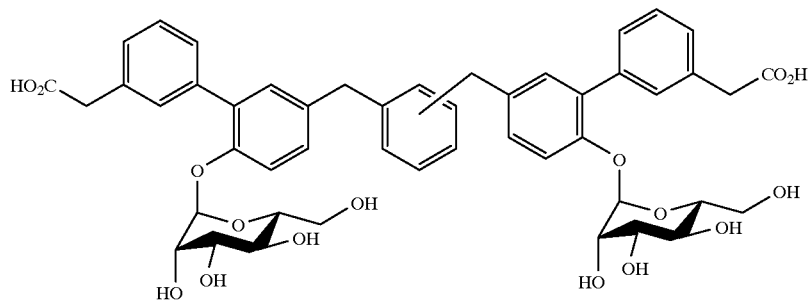
C
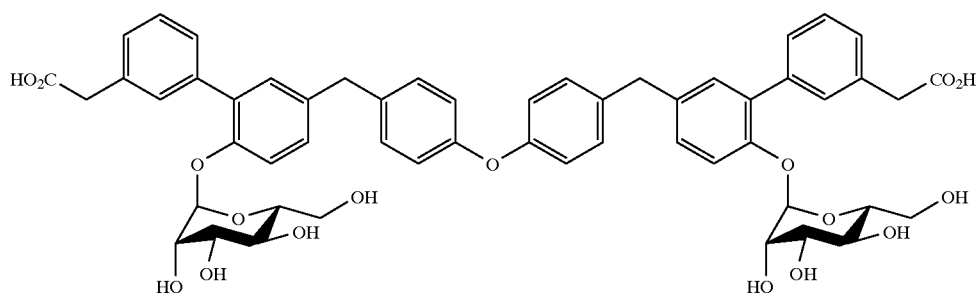
D
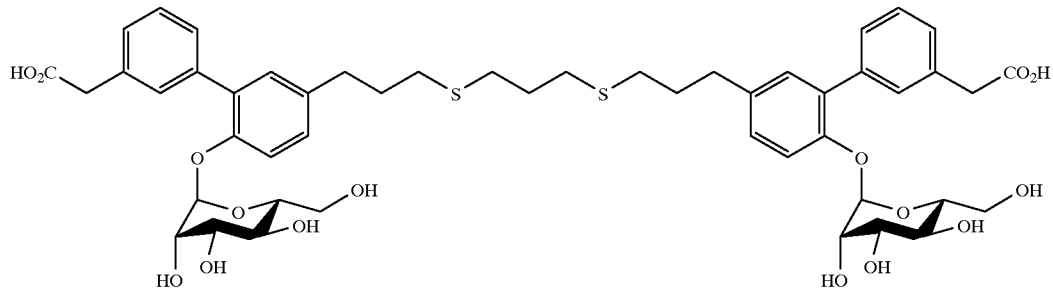
E
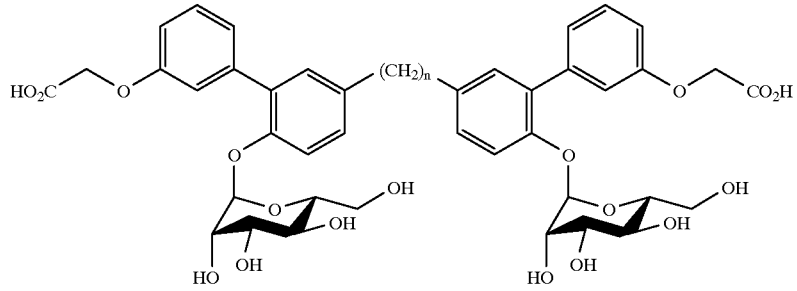

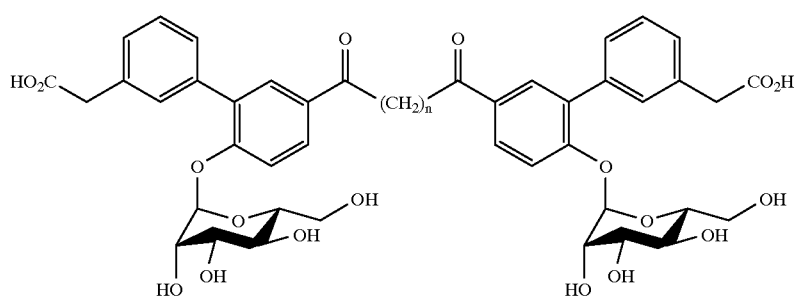

F

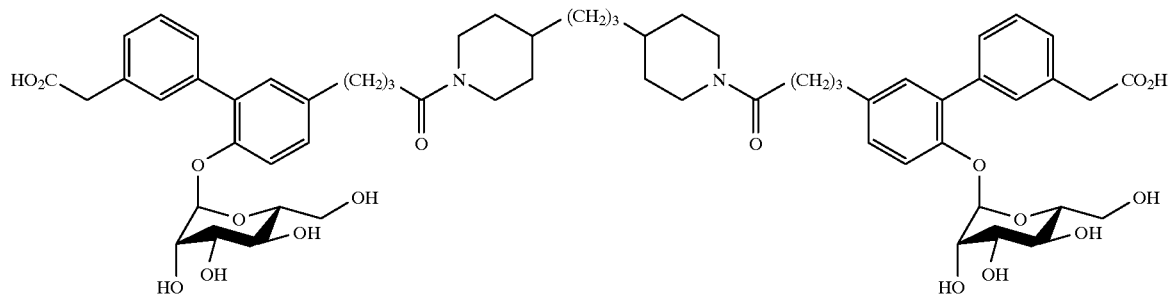

G

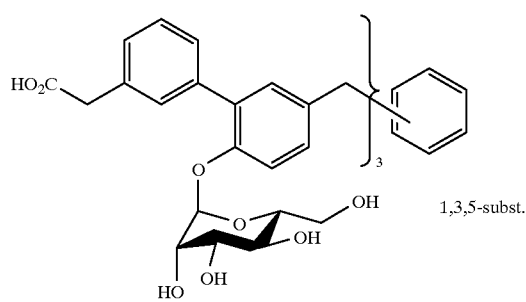

H 1,3,5-subst.

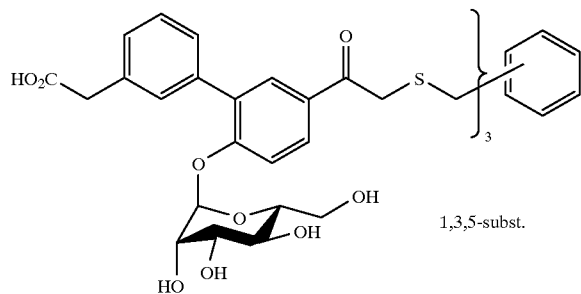

J 1,3,5-subst.

The present invention also provides pharmaceutical compositions comprising a compound of formula II or formula III and a pharmaceutically acceptable carrier.

The present invention further provides a method of inhibiting the binding of E-selectin, P-selectin, or L-selectin to $sLe^x$ or $sLe^a$ comprising the step of administering to a patient an effective amount of a compound having the structure of formula II or formula III to inhibit the binding of E-, P- or L-selectin or P-selectin to $sLe^x$ or $sLe^a$, and a pharmaceutically active composition comprising a compound of formula II or III and a pharmaceutically acceptable carrier.

The compounds of the present invention may be used in methods for treating diseases such as ARDS, Crohn's disease, septic shock, traumatic shock, multi-organ failure, autoimmune diseases, asthma, inflammatory bowel disease, psoriasis, rheumatoid arthritis, reperfusion injury that occurs following heart attacks, strokes, organ transplants, and cancer, which comprises administering to an animal in need of such treatment a therapeutically effective amount of a compound having the formula II or formula III to reduce the symptoms of the disease.

DETAILED DESCRIPTION OF THE PREFERRED EMBODIMENTS

It has been found that compounds having the formula (II) shown above act to inhibit E-, P- or L-selectin binding to $sLe^x$ or $sLe^a$.

As used herein, the term "alkyl" shall mean a monovalent straight chain or branched chain group of 1 to 12 carbon atoms including, but not limited to, methyl, ethyl, n-propyl, isopropyl, n-butyl, sec-butyl, isobutyl, tert-butyl and the like.

The term "lower alkyl" shall mean any alkyl group having from one to six carbon atoms.

The term "halogen" shall mean any atom selected from the group consisting of chlorine, fluorine, bromine, and iodine.

The term "alkoxy" shall mean an alkyl group attached to a molecule through an oxygen atom including, but not limited to, methoxy, ethoxy, isopropoxy, n-butoxy, sec-butoxy, isobutoxy, tert-butoxy and the like.

The term "alkylamino" shall mean groups having the structure —NH—(alkyl), or —N—(alkyl)$_2$, including, for example, methylamino, ethylaamino, isopropylamino and the like.

The term "aryl" shall mean carbocyclic aromatic groups including, but not limited to, phenyl, 1 or 2-naphthyl, fluorenyl, (1,2)-dihydronaphthyl, indenyl, indanyl, thienyl, benzothienyl, thienopyridyl and the like.

The term "aralkyl" (also called arylalkyl) shall mean an aryl group appended to an alkyl group including, but not limited to, benzyl, 1 and 2-naphthylmethyl, halobenzyl, alkoxybenyl, hydroxybenzyl, aminobenzyl, nitrobenzyl, guanidinobenzyl, fluorenylmethyl, phenylmethyl(benzyl), 1-phenylethyl, 2-phenylethyl, 1-naphthylethyl and the like.

The term "hydroxyalky" shall mean —OH appended to an alkyl group.

The term "aminoalkyl" shall mean a group having the structure —NR$_x$R$_y$ appended to an alkyl group. The groups R$_x$ and R$_y$ are independently selected from, for example, hydrogen, alkyl and aryl.

The term "alkyl carboxylic acid" shall mean a carboxyl group (—CO$_2$H) appended to an alkyl group.

The term "alkyl carboxamide" shall mean a group having the formula —CONR$_x$R$_y$ appended to an alkyl group where R$_x$ and R$_y$ are as defined above under arninoalkyl.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of the compounds of the present invention. These salts can be prepared in situ during the final isolation and purification of the compounds or by separately reacting the purified compound in its free form with a suitable organic or inorganic acid or base and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine, and the like. (See, for example S. M. Berge, et al., "Pharmaceutical Salts," *J. Pharm. Sci.*, 66: 1–19 (1977), which is incorporated herein by reference.)

Examples of pharmaceutically acceptable, non-toxic esters of the compounds of this invention include $C_1$ to $C_6$ alkyl esters wherein the alkyl group is a straight or branched chain. Acceptable esters also include $C_5$ to $C_7$ cycloalkyl esters as well arylalkyl esters such as, but not limited to benzyl. $C_1$ to $C_4$ alkyl esters are preferred. Esters of the compounds of the present invention may be prepared according to conventional methods.

Examples of pharmaceutically acceptable, non-toxic amides of compounds of this invention include amides derived from ammonia, primary $C_1$ to $C_6$ alkyl amines and secondary $C_1$ to $C_6$ dialkyl amines wherein the alkyl groups are straight or branched chain. In the case of secondary amines the amine may also be in the form of a 5 or 6 membered heterocycle containing one nitrogen atom. Amides derived from ammonia, $C_1$ to $C_3$ alkyl primary amides and $C_1$ to $C_2$ dialkyl secondary amides are preferred. Amides of the compounds of the invention may be prepared according to conventional methods.

The term "prodrug" refers to compounds that are rapidly transformed in vivo to yield to the parent compound of the above formula, for example by hydrolysis in blood. A thorough discussion is provided in T. Higuchi and V. Stella, "Pro-drugs as Novel Delivery Systems", Vol 14 of the A.C.S. Symposium Series, and in Bioreversible Carriers in Drug Design, ed. Edward B. Roche, American Pharmaceutical Association and Pergamon Press, 1987, both of which are incorporated herein by reference.

The present invention also provides for pharmaceutically active compositions that contain the compounds of the present invention. It is also contemplated that pharmaceutically active compositions may contain a compound of the present invention and other compounds that inhibit or compete with E-selectin or P-selectin binding to sLe$^x$ or sLe$^a$ including sLe$^x$ and sLe$^a$ themselves.

Pharmaceutically active compositions of the present invention comprise a physiological carrier and a compound of formulas II or III.

The pharmaceutical compositions of the present invention may include one or more of the compounds having the above structures II or III formulated together with one or more nontoxic, physiologically acceptable carriers, adjuvants or vehicles, which are collectively referred to herein as carriers, for parenteral injection, for oral administration in solid or liquid form, for rectal or topical administration and the like.

The compositions can be administered to humans and animals either orally, rectally, parenterally (intravenously, intramuscularly, or subcutaneously), intracisternally, intravaginally, intraperitoneally, locally (powders, ointments or drops), or as a buccal or by inhalation (nebulized, or as nasal sprays).

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyol,(propylene glycol, polyethylene glycol, glycerol and the like), suitable mixtures thereof, vegetable oils (such as olive or cannola oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the compounds can be incorporated into slow or timed release or targeted delivery systems such as polymer matrices, liposomes, and microspheres. They may be sterilized, for example, by filtration through a bacteria-retaining filter, or by incorporating sterilizing agents in the form of sterile water, or some other sterile injectable medium immediately before use.

Solid dosage forms for oral administration include capsules, tablets, pills, powders and granules. In such solid dosage forms, the active compound or a pro-drug ester is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions that can be used are polymeric substances and waxes.

The active compounds can also be in microencapsulated form, if appropriate, with one or more of the abovementioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, cannola oil, castor oil and sesame seed oil, glycerol, tetrahydrofurfuryl alcohol, polyethylene glycols and fatty acid esters of sorbitan or mixtures of these substances, and the like.

Besides such inert diluents, the compositions can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth or mixtures of these substances and the like.

Compositions for rectal administrations are preferably suppositories, which can be prepared by mixing the compounds of the present invention with suitable nonirritating excipients or carriers such as cocoa butter, polyethylene glycol or a suppository wax, which are solid at ordinary temperatures but liquid at body temperature and therefore melt in the rectal or vaginal cavity and release the active component.

Dosage forms for topical administration of a compound of this invention include ointments, powders, sprays and inhalants.

The active component is admixed under sterile conditions with a physiologically acceptable carrier and any needed preservatives, buffers or propellants as may be required. Ophthalmic formulations, eye ointments, suspensions, powders and solutions are also contemplated as being within the scope of this invention.

The compounds of this invention can also be administered in the form of liposomes. As is known in the art, liposomes are generally derived from phospholipids or other lipid substances. Liposomes are formed by mono or multilamellar hydrated liquid crystals that are dispersed in an aqueous medium. Any nontoxic, physiologically acceptable and metabolizable lipid capable of forming liposomes can be used. The present compositions in liposome form can contain, in addition to the selectin binding inhibitors of the present invention, stabilizers, preservatives, excipients and the like. The preferred lipids are the phospholipids and the phosphatidyl cholines (lecithins), both natural and synthetic. Methods to form liposomes are well known in the art.

Actual dosage levels of active ingredient in the compositions of the present invention may be varied so as to obtain an amount of active ingredient that is effective to obtain the desired therapeutic response for a particular composition and method of administration. The selected dosage level, therefore, depends on the desired therapeutic effect, on the route of administration, on the desired duration of treatment and other factors.

The total daily dosage of the compounds of this invention administered to a host in single or divided doses may be in the range of about 0.3 mg to about 50 mg per kilogram of body weight. Dosage unit compositions may contain such submultiples thereof as may be used to make up the daily dosage. It will be understood, however, that the specific dose level for any particular patient, whether human or other animal, will depend upon a variety of factors including the body weight, general health, sex, diet, time and route of administration, rates of absorption and excretion, combination with other drugs and the severity of the particular disease being treated.

In particular, the compounds of the present invention may be used to treat a variety of diseases relating to inflammation and cell-cell recognition and adhesion. For example, the compounds of the present invention may be administered to a patient to treat septic shock, chronic inflammatory diseases such as psoriasis and rheumatoid arthritis, and reperfusion tissue injury that occurs following heat attacks, strokes and organ transplants, traumatic shock, multi-organ failure, autoimmune diseases, asthma and inflammatory bowel disease. In each case, an effective amount of the compounds of the present invention is administered either alone or as part of a pharmaceutically active composition to a patient in need of such treatment. It is also recognized that a combination of the compounds may be administered to a patient in need of such administration. The compounds of the present invention may also be administered to treat other diseases that are associated with cell-cell adhesion. As the present compounds inhibit the binding of E-selectin or P-selectin with $sLe^x$ or $sLe^a$, any disease that is related to this interaction may potentially be treated by the inhibition of this binding interaction.

In addition to being found on some white blood cells, $sLe^a$ is found on various cancer cells, including lung and colon cancer cells. It has been suggested that cell adhesion involving $sLe^a$ may be involved in the metastasis of certain cancers and that inhibitors of $sLe^a$ binding might be useful in the treatment of some forms of cancer.

Many of the compounds of the present invention may be synthesized according to the following general synthetic schemes.

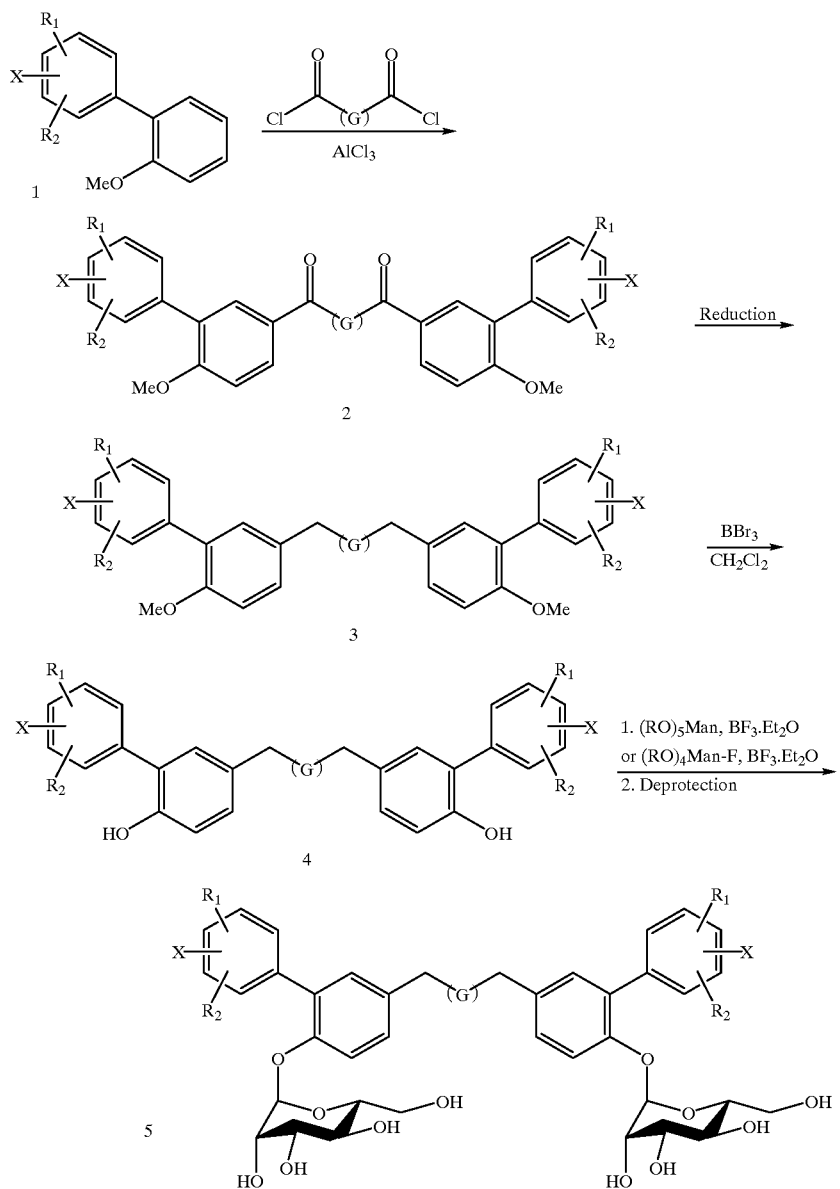

SCHEME 1

In this scheme, a substituted biphenyl (1, U.S. Pat. No. 5,444,050) is reacted with a diacid chloride which gives the diaryldione 2. Preferred examples include linear and branched diacid chlorides of five to 16 carbons and aryl and aralkyl diacid chlorides. These compounds can be reduced by one of a number of ways known to those skilled in the art, namely catalytic hydrogenation, Wolff-Kishner reduction, metal hydrides such as triethyl silane, or Clemmensen reduction. The resulting compounds (3) are converted to the phenol 4 by the action of boron tribromide in a halogenated solvent, preferably at 0° C. to rt. Glycosylation using a protected mannose unit in the presence of boron trifluoride etherate, followed by base hydrolysis provides the desired compound 5.

a carboxylic acid. For example, in this scheme, a compound such as 4-(4-methoxyphenyl)butanoic acid is converted to an acid chloride using thionyl chloride, followed by a Friedel-Crafts reaction with anisole to provide ketone 7. Reduction of the ketone by any one of a number of different methods known to those skilled in the art provides compound 8. Lithiation ortho to the methoxy groups, followed by conversion to the boronic acid and palladium-mediated

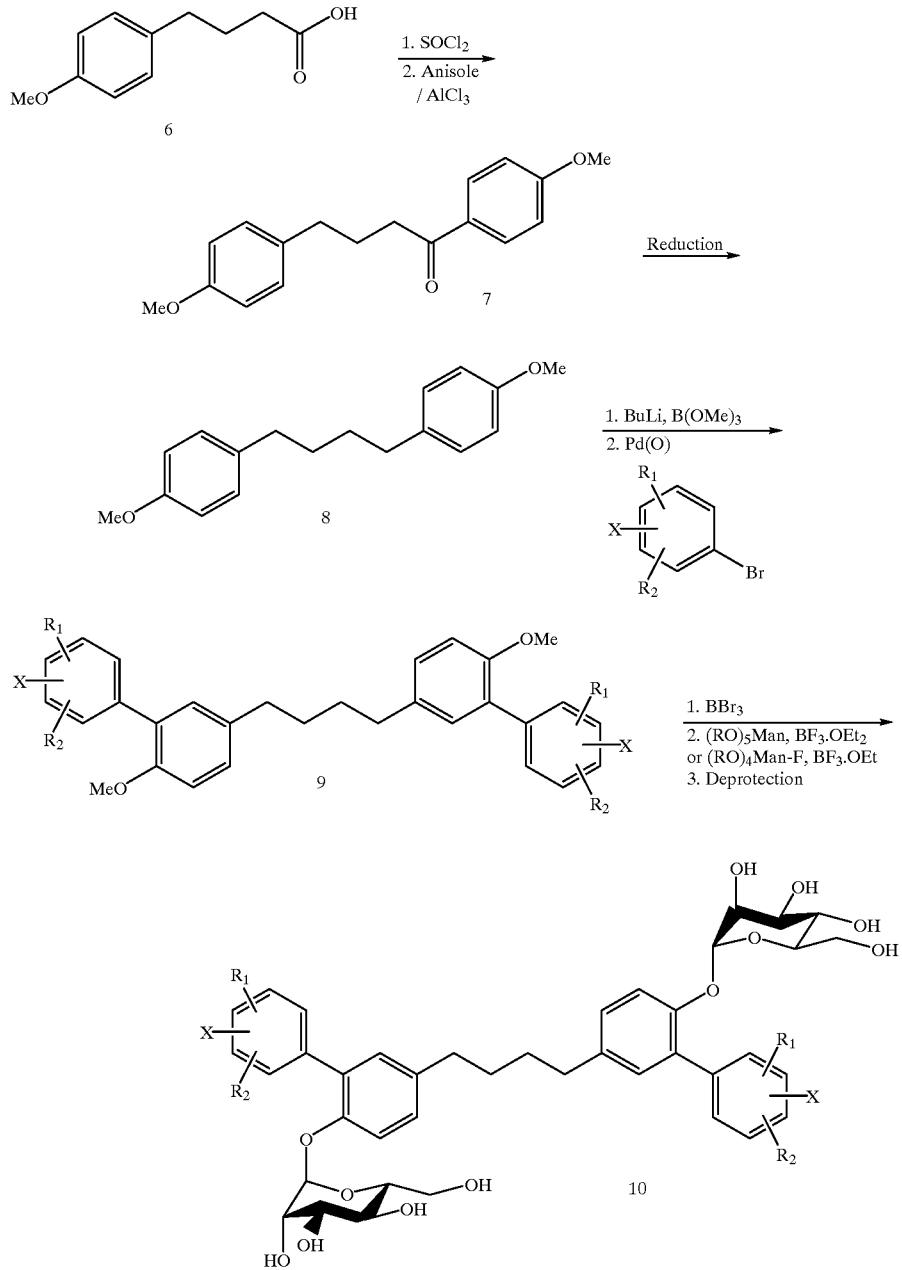

SCHEME 2

It can be desirable in certain cases to construct the linker between the two rings which are later substituted with the mannose unit prior to the attachment of the ring which bears biaryl coupling gives 9. Demethylation of the ethers followed by glycosylation and deprotection gives the target compound 10.

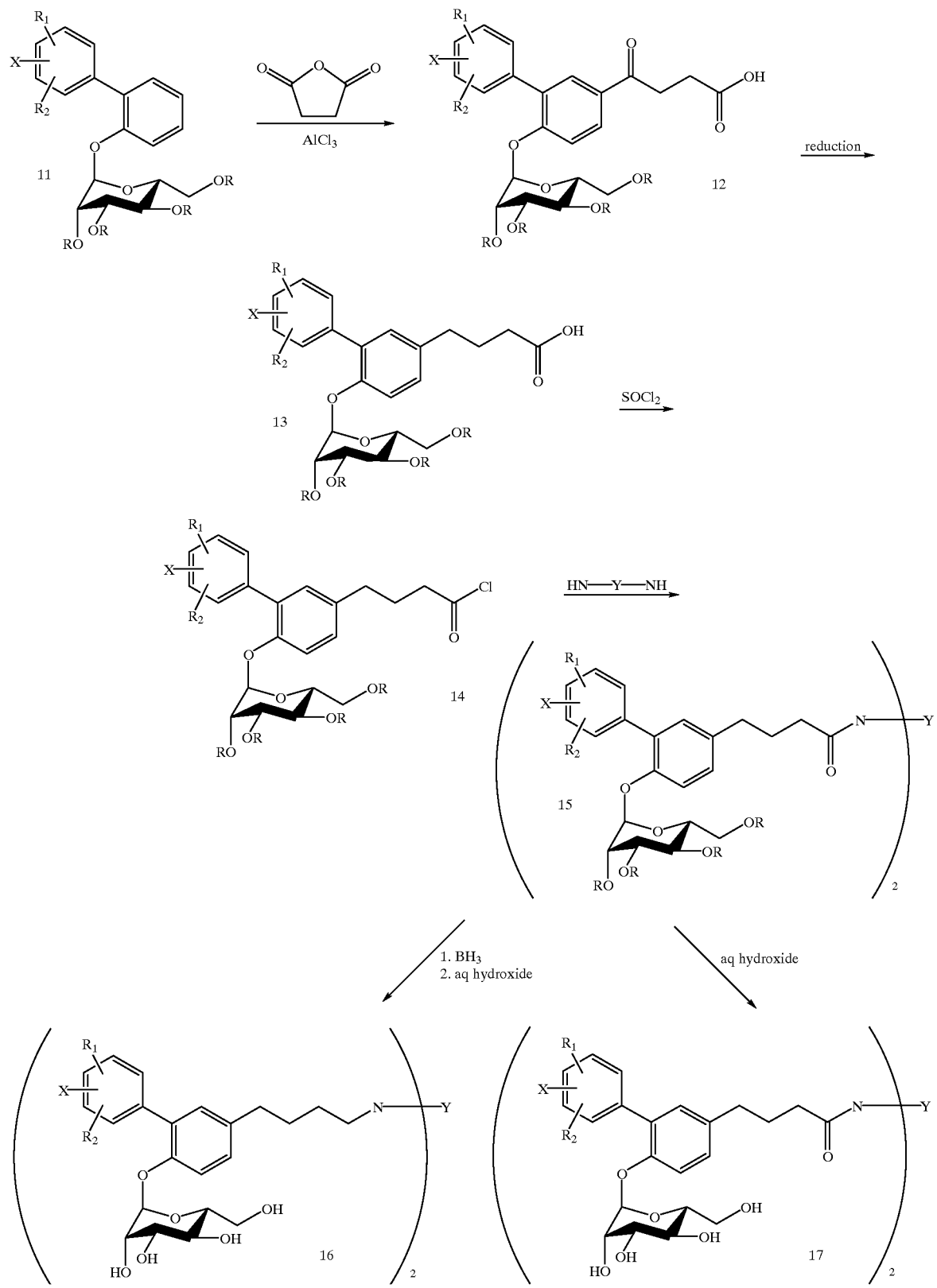

In other instances, it may be advantageous to perform the Friedel-Crafts reaction on a compound such as 11 (U.S. Pat. No. 5,444,050) in which the sugar moiety is already in place. For example, 11 can be treated with succinic anhydride in the presence of a Lewis acid such as aluminum chloride to provide the keto acid 12. Reduction of the ketone by one of a number of ways known to those skilled in the art provides the acid 13, which is converted to the acid chloride 14 using thionyl chloride in a halogenated solvent at low temperature, or another suitable method. The acid chloride is allowed to react with one of a number of primary or secondary amines, especially diamines like ethylenediamine, piperazine, homopiperazine, 4,4'-trimethylenedipiperidine, or other alkyl diamine, giving multimeric compounds such as 15. Reduction of the amides using borane or another suitable reagent in an oxygenated solvent at low temperature, followed by hydrolysis of the protective groups gives the desired compound 16. Furthermore, amides 15 can be hydrolyzed directly to provide amides 17.

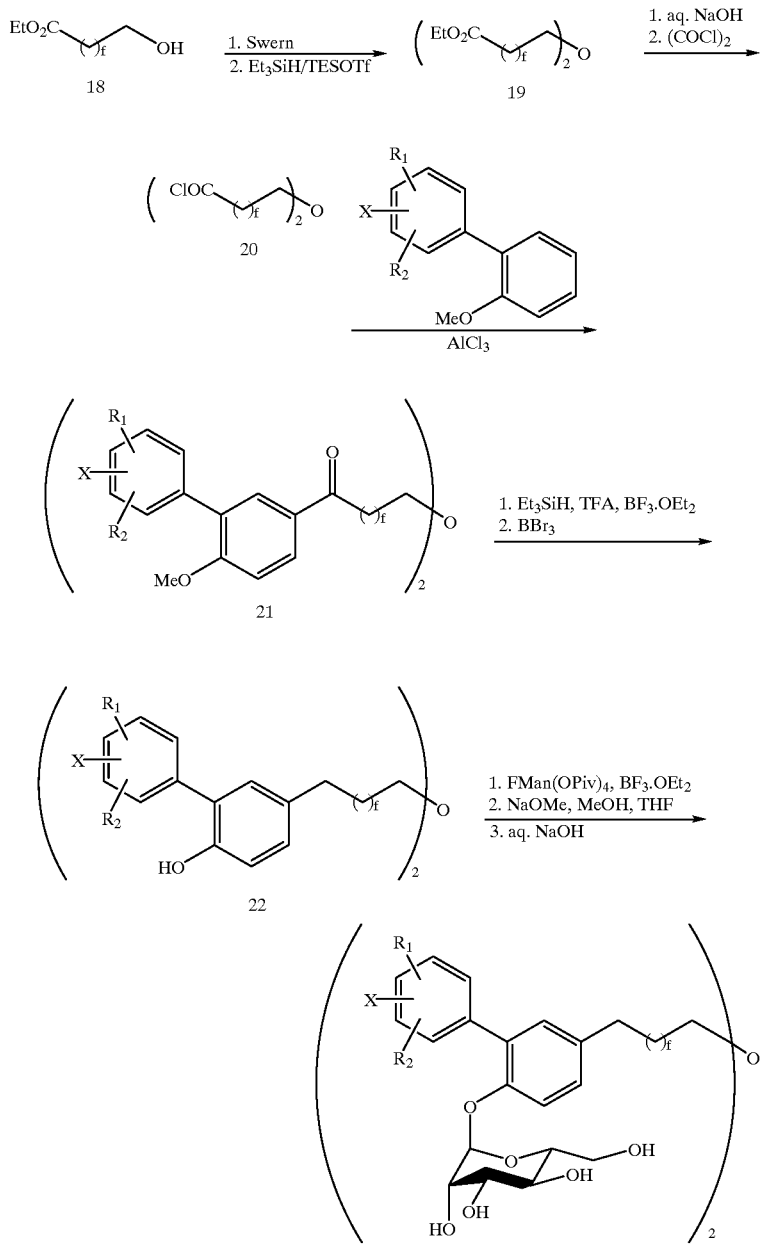

SCHEME 4

Compounds containing ether linkages can be prepared as in Scheme 4. Oxidation of hydroxyesters (18) to the aldehydes followed by self condensation gives the ethers (19), which are converted to the acid chlorides (20). Friedel-Crafts coupling, reduction, demethylation, glycosylation and deprotection leads to the ethers (23).

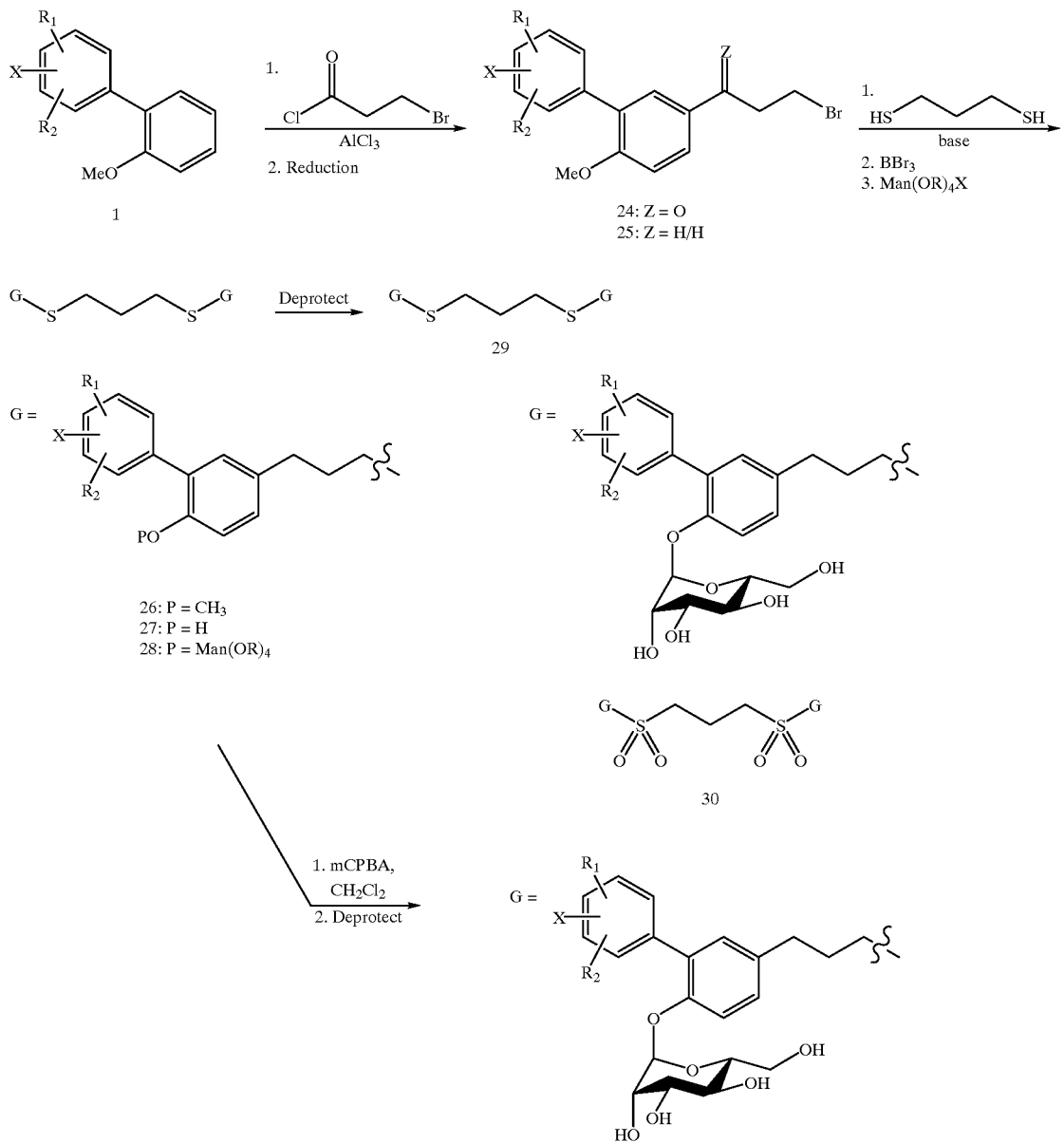

SCHEME 5

In some instances, it may be desirable to prepare other compounds by the sequence of reactions shown in Scheme 5. Thus, 1 may undergo a Friedel-Crafts reaction with other halogenated acid halides, for example 3-bromopropionyl chloride, to give 24. Reduction of the benzylic ketone can be accomplished by one of a number of methods known to those skilled in the art to provide halide 25. Reaction of 25 with 1,3-propane dithiol, or other suitable disulfide in the presence of a suitable base gives compound 26. Demethylation can be accomplished by one of a number of methods, especially boron tribromide in a halogenated solvent at low temperature, which provides phenol 27. The phenol is reacted with a protected mannopyranoside using boron trifluoride etherate in a halogenated solvent, and the protective groups are removed with aqueous base which gives compound 29. Alternatively, the glycoside 28 can be treated with a suitable oxidizer such as m-chloroperoxybenzoic acid in the appropriate solvent which gives the sulfone. Treatment with aqueous base gives the final compound 30.

Scheme 6
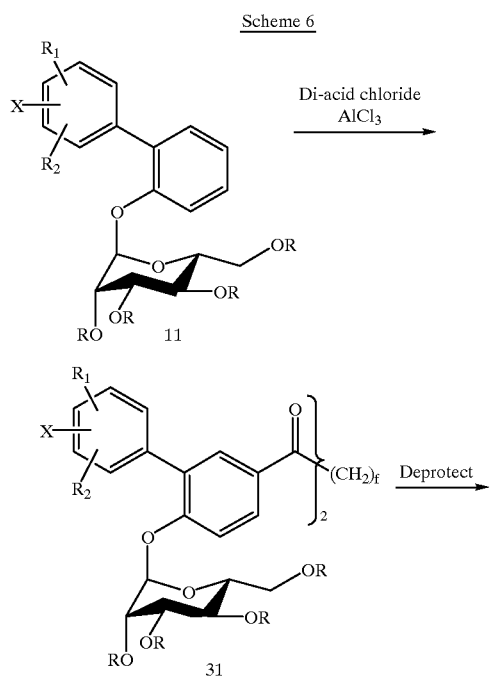
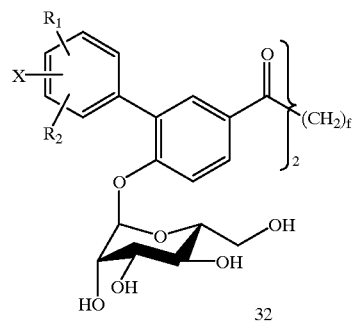
In still other instances, intermediate 11 undergoes a Friedel-Crafts reaction with a di-acid chloride in halogenated solvent in the presence of aluminum chloride or other suitable Lewis acid, to give 31. Deprotection of the mannose moiety using aqueous hydroxide or methoxide followed by hydroxide gives the final compound 32.
SCHEME 7
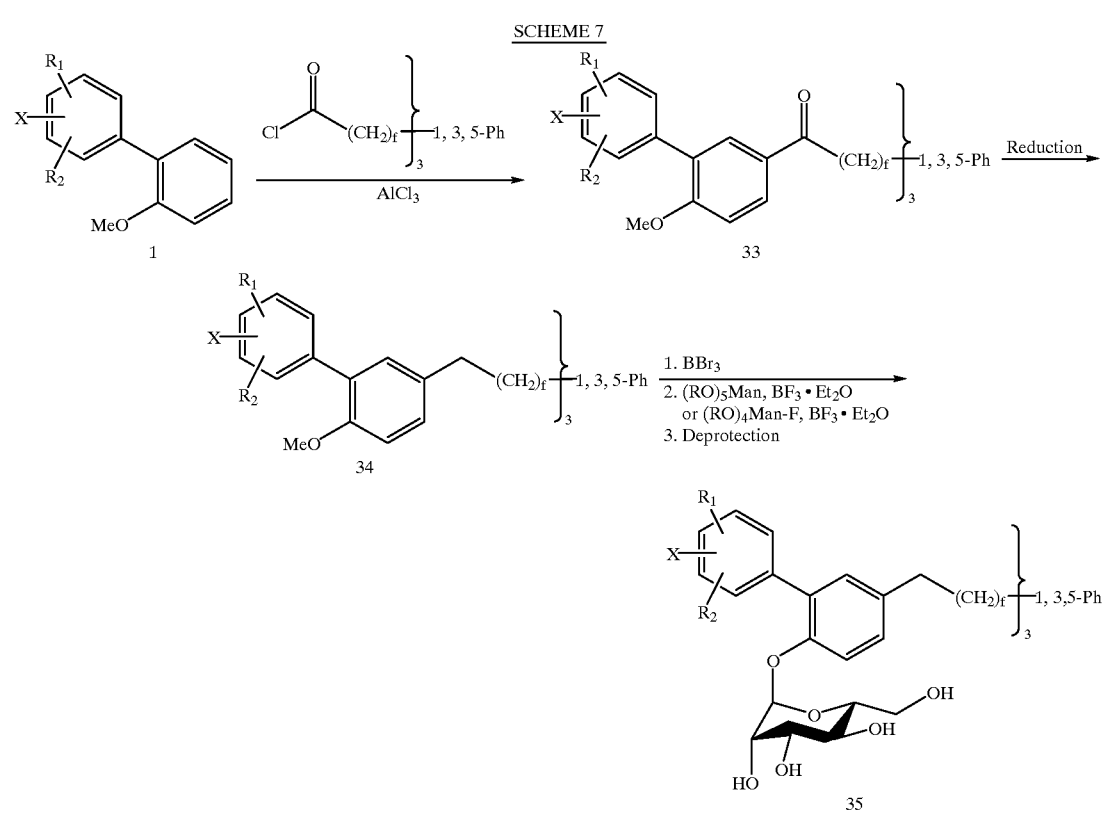

In this scheme, a substituted biphenyl (1, U.S. Pat. No. 5,444,050) is reacted with a triacid chloride to give the benzylic ketone 33. These ketones can be reduced by one of a number of ways known to those skilled in the art and listed in Scheme 1. The resulting compounds (34) can be demethylated, glycosylated, and deprotected to provide the desired compounds 35.

NMR (400 MHz, CDCl$_3$): 7.96 (dd, J=6.6, 1.9 Hz, 2H), 7.92 (d, J=1.9 Hz, 2H), 7.42 (m, 2H), 7.34 (t, J=6 Hz, 2H), 7.18–7.28 (m, 4H), 7.00 (d, J=6.3 Hz, 2H), 3.87 (s, 6H), 3.69 (s, 6H), 3.68 (s, 4H), 3.01 (m, 4H), 1.84 (m, 4H) ppm. IR (NaCl): 1741, 1677 cm$^{-1}$.

Step 2

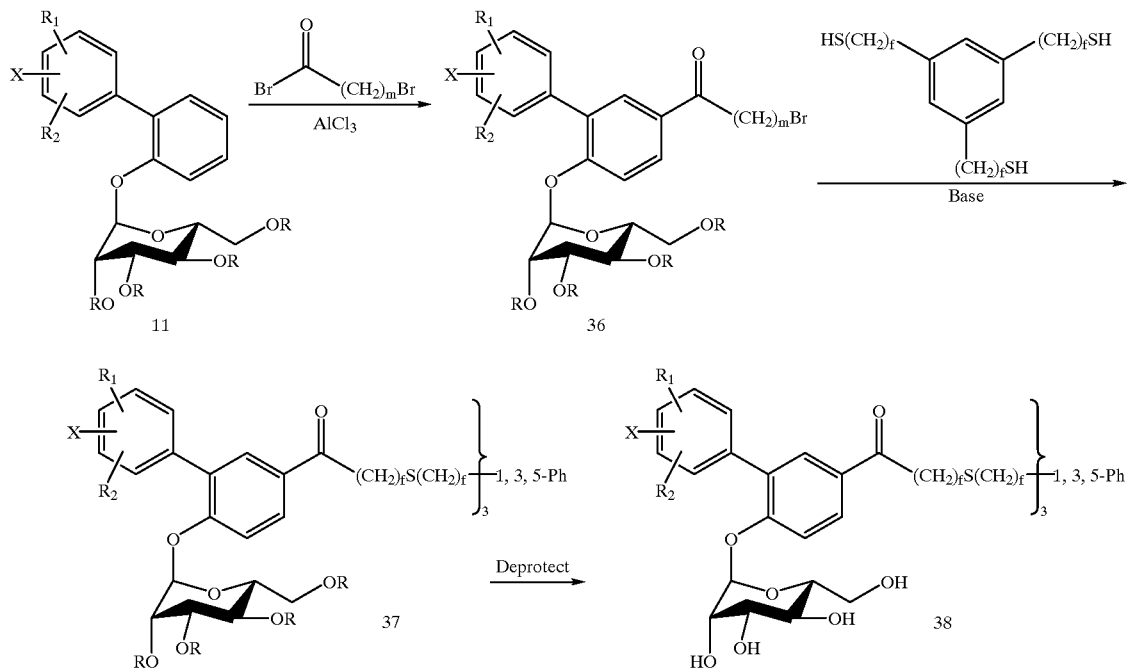

SCHEME 8

In a similar fashion, 11 can undergo a Friedel-Crafts reaction with bromoalkyl acid bromide to provide 36. Reaction of the bromo ketone with a 1,3,5-substituted benzene trithiol in the presence of a base provides the compounds 37. Hydrolysis of the protective groups gives the desired compounds (38).

The present invention is illustrated by the following representative examples:

EXAMPLE 1

1,6-Bis-[3-(3-carboxymethylphenyl)-4-(2-α-D-mannopyranosyloxy)phenyl]hexane

Step 1

Adipoyl chloride (2.0 g, 10.9 mmol) was dissolved in 1,2-dichloroethane (55 mL) and cooled in an ice bath. Aluminum chloride (5.8 g, 43.5 mmol) was added followed by 3-(2-methoxyphenyl)phenylacetic acid methyl ester (5.75 g, 22.4 mmol) [T. P. Kogan, B. Dupré, I. L. Scott, K. Keller, H. Dao and P. Beck, U.S. Pat. No. 5,444,050 and T. P. Kogan, B. Dupré, K. M. Keller, I. L. Scott, H. Bui R. V. Market, P. J. Beck, J. A. Voytus, B. M. Revelle and D. Scott, *J Med Chem*, 1995, 38, 4976–4984] and the mixture was stirred at rt for 30 min, then mixed with ice water (30 mL). The organic materials were isolated, and the aqueous portion was extracted with dichloromethane (3×5 mL). The organic materials were combined, dried (MgSO$_4$) then concentrated under reduced pressure. The residue was purified by flash chromatography (SiO$_2$, gradient elution from hexane to 3:1 hexane/ethyl acetate) to give the product 2 (2.23 g, 33%). $^1$H Part A: The product from step 1 (2.23 g, 3.6 mmol) was dissolved in acetonitrile and treated with lithium hydroxide solution (0.8 g, 18 mmol lithium hydroxide monohydrate in 8 mL water). The mixture was stirred at room temperature overnight then acidified to pH 4 with 2N HCl, and extracted with ethyl acetate. The extracts were combined, dried (MgSO$_4$) then concentrated under reduced pressure. IR (NaCl): 1711, 1677 cm$^{-1}$.

Part B: The keto acid from part A (1.86 g, 3.1 mmol) was dissolved in dimethylsulfoxide (15 mL) and mixed with hydrazine (1.0 mL, 31 mmol). This mixture was heated at 80° C. under nitrogen for 2.5 hours, then cooled. Potassium t-butoxide (3.5 g, 31 mmol) was added and the mixture was again heated at 80° C. overnight, then mixed with water (30 mL) and acidified with 2N HCl, and extracted with ethyl acetate. The extracts were combined, dried (MgSO$_4$) and concentrated under reduced pressure to give 3 (1.6 g, 91%). IR (NaCl): 1713 cm$^{-1}$.

Step 3

Part A: The diacid from step 2, part B (1.6 g, 2.8 mmol) was dissolved in dichloromethane (14 mL) under nitrogen, and chilled in a dry-ice/2-propanol bath. Boron tribromide (1.4 mL, 14 mmol) was added slowly; the mixture was stirred at room temperature for 2 hours, then mixed with ice-water (25 mL). The organic material was separated, washed with saturated sodium bicarbonate solution (20 mL), water (20 mL), saturated sodium chloride (20 mL) then dried (MgSO$_4$) and concentrated under reduced pressure to give 2.38 g of the crude product.

Part B: The residue from part A was mixed with methanol (50 mL) and sulfuric acid (5 drops) was added. The mixture was heated at reflux overnight, then concentrated under reduced pressure. The residue was dissolved in dichloromethane (50 mL) and treated with sodium carbonate, then filtered through a pad of silica gel. The filtrate was concentrated under reduced pressure, and the residue was purified by flash chromatography (SiO$_2$, gradient elution, hexane to 3:1 hexane/ethyl acetate) to give 1,6-bis-(3-(3-carbomethoxymethylphenyl)-4-hydroxyphenyl)hexane (0.9 g, 38%). $^1$NMR (400 MHz, CDCl$_3$): 6.80–7.50 (m, 14H), 3.70 (s, 6H), 3.68 (s, 4H), 2.55 (dd, J=5.5, 5.5 Hz, 4H), 1.59 (m, 4H), 1.36 (m, 4H) ppm. IR (NaCl): 3430, 1731 cm$^{-1}$.

Step 4

1,6-Bis-(3-(3-carbomethoxymethylphenyl)-4-hydroxyphenyl)hexane (0.9 g, 1.6 mmol) was dissolved in 1,2-dichloroethane (8 mL). α-D-Mannose pentaacetate (1.9 g, 4.8 mmol) was added in one portion, then boron trifluoride etherate (2.5 mL, 19.2 mmol) was added slowly. The mixture was stirred under nitrogen overnight at room temperature then mixed with water (15 mL). The organic material was separated and the aqueous portion was extracted with dichloromethane (3×2 mL). The extracts were combined with the original organic fraction, dried (MgSO$_4$) then concentrated under reduced pressure. The residue was purified by flash chromatography (SiO$_2$, gradient elution hexane to 3:1 hexane/ethyl acetate) to provide 1,6-bis-[3-(3-carbomethoxymethylphenyl)-4-(tetra-O-acetyl-α-D-mannopyranosyl)oxyphenyl]hexane (1.5 g, 77%). $^1$H NMR (400 MHz, CDCl$_3$): 7.31–7.37 (m, 6H), 7.19–7.24 (m, 4H), 7.09–7.13 (m, 4H), 5.25 (d, J=0.6 Hz, 2H), 3.57–3.66 (m, 6H), 3.3–3.50 (m, 10H), 2.54 (m, 4H), 1.58 (m, 4H), 1.34 (m, 4H) ppm. IR (NaCl): 1752 cm$^{-1}$.

Step 5

The glycoside from step 4 (1.5 g, 1.2 mmol) was dissolved in acetonitrile (6 mL), and treated with a solution of lithium hydroxide monohydrate (1.0 g, 24 mmol) in water (10 mL). The mixture was stirred at room temperature overnight then acidified to pH 2 with concentrated hydrochloric acid. The mixture was concentrated under reduced pressure and the residue was purified by HPLC (reverse-phase, gradient elution 5–50% acetonitrile in water, monitored at 254 nm) to give 1,6-bis-[3-(3-carboxymethylphenyl)-4-(2-α-D-mannopyranosyloxy)phenyl]hexane, (5), (0.35 g, 33%) as a white solid, mp 115–117° C.; $^1$H NMR (400 MHz, DMSO-d$_6$): 7.31–7.37 (m, 6H), 7.19–7.24 (m, 4H), 7.09–7.13 (m, 4H), 5.25 (d, J=0.6 Hz, 2H), 3.57–3.66 (m, 6H), 3.3–3.50 (m, 10H), 2.54 (m, 4H), 1.58 (m, 4H), 1.34 (m, 4H) ppm. IR (KBr): 3420, 1711 cm$^{-1}$.

EXAMPLE 2

1,6-Bis-[3-(3-carboxymethylphenyl)-4-(2-α-D-mannopyranosyloxy)phenyl]hexane, disodium salt (alternative method)

Step 1

Adipoyl chloride (16.8 mL, 112 mmol) and 3-(2-methoxyphenyl)phenylacetic acid methyl ester (60.9 g, 225 mmol) were dissolved in dichloromethane (300 mnL) and cooled at 0° C. Aluminum chloride (67.7 g, 507 mmol) was added, stirred at 0° C for 5 minutes then quenched with ice. The product was extracted with EtOAc (1 L), washed with water (500 mL), sat. NaHCO$_3$ (50 mL) and sat. NaCl (50) mL). The solution was dried over Na$_2$SO$_4$, filtered through a plug of magnesium sulfate, concentrated, then recrystallized from ether/ethyl acetate to provide 2, (64.7 g, 89%).

Step 2

The bis-ketone 2 (15 g, 23.1 mmol) was dissolved in hot EtOAc:EtOH (4:1, 100 mL). The resulting solution was cooled, trifluoroacetic acid (1 ml) and Pearlman's catalyst (0.75 g) were added. The mixture was shaken under a hydrogen atmosphere (50 psi) for 18 h, and filtered through a pad of celite. The solution was washed with sat. NaHCO$_3$, water and sat. brine, dried (Na$_2$SO$_4$), filtered through MgSO$_4$ and concentrated. Toluene was evaporated from the product to remove EtOAc, and the residue was dried under high vacuum to give 1,6-bis-[3-(3-carboethoxymethylphenyl)-4-methoxyphenyl]hexane quantitatively.

Step 3

The bis-methyl ether (25.6 g, 41 mmol) was dissolved in dichloromethane (165 mL) and cooled to 0° C. Boron tribromide in dichloromethane (33 mL) was added slowly, then the cooling bath was removed, and the reaction was stirred at rt for 20 min. The reaction mixture was cooled in an ice bath, the nitrogen atmosphere inlet replaced with a CaCl$_2$ drying tube and ethanol (35 mL) added dropwise. The mixture was poured onto ice and extracted with EtOAc. The organic material was separated, washed with water, brine, dried (MgSO$_4$) and concentrated under reduced pressure to give 1,6-bis-[3-(3-carboethoxymethylphenyl)-4-hydroxyphenyl]hexane (24.2 g, 100%).

Step 4

To an ice-cold solution of the bis-phenol (25.37 g, 42.7 mmol) and tetra-O-pivaloyl-α-D-mannopyranosyl fluoride (66.4 g, 128 mmol) [I. L. Scott and T. P. Kogan, U.S. patent application filed May 20, 1996, entitled "High Yield Stereospecific Mannosylation"] in dichloromethane (427 mL) was added BF$_3$.OEt$_2$ (47.3 mL, 384 mmol) dropwise and the ice-cold mixture stirred for 1 h. The mixture was diluted with EtOAc and washed with water (2×), sodium hydroxide (2M), water and sat. sodium chloride, dried over magnesium sulfate and concentrated under reduced pressure. Purification by chromatography (silica, eluted with a hexane/EtOAc gradient 30:1 to 6:1) gave 1,6-bis-[3-(3-carboethoxymethylphenyl)-4-(tetra-O-pivaloyl-α-D-mannopyranosyloxy)phenyl]hexane (59.8 g, 89%).

Step 5

Part A: To a solution of the bis-glycoside in THF (24 mL) was added methanol (24.4 mL) followed by an ice-cold solution of freshly prepared sodium methoxide (from sodium, 0.5 g, 22 mmol) in methanol (24.4 mL), and the mixture was stirred at rt overnight. The precipitate was collected by filtration and washed with a small volume of THF/methanol (2:1, 2×) then acetone. The solid sodium alkoxide (6.3 g) was purified further by stirring with acetone and filtering.

Part B: The precipitate was stirred in water (27 mL) at rt for 30 minutes. The pH was then adjusted to 14 and maintained at pH 14 using the minimum amount of sodium hydroxide (2M) while stirring. After 4 hours deprotection was complete by reverse phase HPLC. The solution was neutralized with pre-washed ion exchange resin (Dowex 50, hydrogen form) and filtered through celite. The solution was then lyophilized to give 1,6-bis-[3-(3-carboxymethylphenyl)-4-(2-α-D-mannopyranosyloxy) phenyl]hexane, disodium salt as a slightly hygroscopic white powder, (6.0 g, 90%), mp 243–245° C.; $^1$H NMR (400 MHz, D$_2$O) 7.64 (s, 2H), 7.58 (d, J=7.7 Hz, 2H), 7.49 (t, J=7.5 Hz, 2H), 7.37 (d, J=8.4 Hz, 2H), 7.19 (d, J=7.3 Hz, 2H), 7.12 (s, 2H), 7.07 (d, J=8.0 Hz, 2H), 5.66 (s, 2H), 4.27 (s, 2H), 4.00–4.20 (m, 4H), 4.04 (dd, J=12.1 and 3.3 Hz, 2H), 3.80–3.92 (m, 6H), 3.72 (d, J=9.2 Hz, 2H), 2.52 (m, 4H), 1.60 (br, 4H), 1.39 (br, 4H); $^{13}$C NMR (100 MHz, D$_2$O) 180.9, 151.5, 138.4, 137.5, 137.4, 132.5, 130.9, 129.1, 129.0, 128.9, 127.3, 117.2, 100.2, 74.2, 70.9, 66.6, 60.9, 45.5, 32.3, 31.6, 29.5; Found: 57.54% C, 5.98% H, 5.12 Na: calc. for $C_{46}H_{52}O_{16}Na_2O3H_2O$: 57.50% C, 6.08% H, 4.78 Na.

EXAMPLE 3

1,4-Bis-[3-(3-carboxymethylphenyl)-4-(2-α-D-mannopyranosyloxy)phenyl]butane

Step 1

4-(4-Methoxyphenyl)butyric acid (2.0 g, 10.3 mmol) was treated with thionyl chloride (20 mL). The reaction was stirred at rt for 3 h, heated at 65° C. overnight and then concentrated under reduced pressure to give 4-(4-methoxyphenyl)butyryl chloride (2.3 g) as a yellow oil which was used without farther purification. IR (NaCl): 1795, 1510, 1244 $cm^{-1}$.

The crude acid chloride (2.07 g, 9.7 mmol) and anisole (1.26 g, 11.6 mmol) were dissolved in 1,2-dichloroethane (32 mL) and chilled in an ice bath. The mixture was treated with aluminum chloride (3.9 g, 29.1 mmol) in portions, stirred for 5 minutes, then mixed with ice water (50 mL). The mixture was extracted with dichloromethane (3×10 mL), and the extracts were combined, washed with saturated sodium chloride (100 mL), dried ($MgSO_4$), then concentrated under reduced pressure. The residue was flushed through silica gel with 10:1 hexane/ethyl acetate then concentrated to give 1,4-bis-(4-methoxyphenyl)butan-1-one (2.49 g, 82%). $^1$H NMR (400 MHz, $CDCl_3$): 7.90 (d, J=8.8 Hz, 2H), 7.11 (d, J=8.4 Hz, 2H), 6.91 (d, J=8.8 Hz, 2H), 6.83 (d, J=8.4 Hz, 2H), 3.86 (s, 3H), 3.78 (s, 3H), 2.90 (t, J=7.3 Hz, 2H), 2.65 (t, J=7.7 Hz, 2H), 2.02 (m, 2H) ppm. IR (NaCl): 1674, 1602, 1244 $cm^{-1}$.

Step 2

The ketone (2.49 g, 8.8 mmol) was dissolved in dichloromethane (30 mL) and treated with trifluoroacetic acid (2.7 mL, 35.2 mmol), triethylsilane (2.8 mL, 17.6 mmol) then boron trifluoride etherate (4.4 mL, 35.2 mmol). The mixture was stirred at room temperature for 2 hours then cooled in an ice bath and mixed with water (50 mL). The mixture was extracted with dichloromethane (3×5 mL) and the organic fractions were combined, washed with saturated sodium chloride (100 mL) and dried ($MgSO_4$), then concentrated under reduced pressure. The residue was flushed through silica gel with 10:1 hexane/ethyl acetate and concentrated to provide 1,4-bis-(4-methoxyphenyl)butane (2.0 g, 85%) as a clear oil. $^1$H NMR (400 MHz, $CDCl_3$): 7.07 (d, J=8.4 Hz, 4H), 6.81 (d, J=8.4 Hz, 4H), 3.78 (s, 6H), 2.56 (m, 4H), 1.61 (m, 4H) ppm. IR (NaCl): 1605, 1248 $cm^{-1}$.

Step 3

1,4-Bis-(4-methoxyphenyl)butane (1.78 g, 6.6 mmol) and TMEDA (4.0 mL, 26.5 mmol) were mixed with anhydrous ether (30 mL) and chilled in an ice bath. n-Butyl lithium (1 0.5 mL of a 2.5M solution, 26.5 mmol) was added and the mixture was warmed to room temperature and stirred for 1 h. The reaction mixture was cooled to 0° C. and treated with trimethyl borate (3.0 mL, 26.5 mmol). The mixture was stirred at room temperature overnight, quenched with 2N HCl (to pH 2) and stirred for an hour. The organic phase was separated and the aqueous portion was extracted with ethyl acetate (3×5 mL). The extracts were combined with the original organic fraction and dried ($MgSO_4$), then concentrated under reduced pressure, to give the boronic acid (3.0 g) which was used without further purification. IR (NaCl): 1603, 1490, 1416, 1328, 1234 $cm^{-1}$.

The crude boronic acid and methyl 3-bromophenyl acetate (3.8 g, 16.8 mmol) were mixed with dimethoxyethane (30 mL) and degassed under nitrogen. The mixture was treated with tribasic potassium phosphate (10.7 g, 50.5 info) and bis(triphenylphosphine)palladium(II) chloride (100 mg, 0.17 mmol). The mixture was degassed again, then heated at reflux for 2 h, cooled to room temperature and mixed with water (100 mL). The mixture was extracted with dichloromethane (3×10 mL) and the extracts were combined, washed with water (50 mL), saturated sodium chloride (50 mL), dried ($MgSO_4$) and concentrated under reduced pressure. The residue was purified by flash chromatography ($SiO_2$, gradient elution, 8:1 hexane/ethyl acetate to 4:1 hexane/ethyl acetate) to give 1,4-bis-[3-(3-carbomethoxymethylphenyl)-(4-methoxy)phenyl]butane (1.14 g, 24%) as a clear oil. $^1$H NMR (400 MHz, $CDCl_3$): 7.41–7.44 (m, 4H), 7.34 (t, J=7.7 Hz, 2H), 7.21–7.60 (m, 2H), 7.08–7.13 (m, 4H), 6.87 (d, J=8.0 Hz, 2H), 3.77 (s, 6H), 3.68 (s, 6H), 3.66 (s, 4H), 2.61 (m, 4H), 1.67 (m, 4H) ppm. IR (NaCl): 1737, 1606, 1239 $cm^{-1}$.

Step 4

1,4-Bis-[3-(3-carbomethoxymethylphenyl)-(4-methoxy)phenyl]butane (0.9 g, 1.6 mmol) was dissolved in dichloromethane (3.0 mL), cooled in a dry ice bath, and treated with boron tribromide (1.2 mL, 12.8 mmol). The mixture was stirred at −78° C. for three hours then placed in a freezer at −10° C overnight. The reaction was quenched with ice water (10 mL) and extracted with dichloromethane (3×5 mL). The organic materials were combined, washed with water (25 mL), saturated sodium chloride (25 mL), dried ($MgSO_4$) then concentrated under reduced pressure. The residue was purified by flash chromatography ($SiO_{2,\ 5:1}$ hexane/ethyl acetate) to give 1,4-bis-[3-(3-carbomethoxymethylphenyl)-4-hydroxyphenyl]butane (0.4 g, 47%). $^1$H NMR (400 MHz, $CDCl_3$): 7.42 (d, J=7.4 Hz, 2H), 7.35–7.38 (m, 4H), 7.27–7.32 (m, 2H), 7.02–7.05 (m, 4H), 6.87 (d, J=8.0 Hz, 2H), 5.12 (s, 2H), 3.70 (s, 6H), 3.68 (s, 4H), 2.59 (m, 4H), 1.65 (m, 4H) ppm. IR (NaCl): 3439, 1732, 1606, 1263 $cm^{-1}$.

Step 5

1,4-Bis-[3-(3-carbomethoxymethylphenyl)-4-hydroxyphenyl]butane (0.4 g, 0.74 mmol) and α-D-mannose pentaacetate (0.72 g, 1.85 mmol) were dissolved in dichloroethane (4.0 mL) and treated with boron trifluoride etherate (1.1 mL, 8.9 mmol). The mixture was stirred at room temperature overnight then quenched with water (10 mL), and extracted with dichloromethane (3×4 mL). The organic materials were combined, washed with water (15 mL), saturated sodium chloride (20 mL), dried ($MgSO_4$) and concentrated under reduced pressure. The residue was purified by flash chromatography ($SiO_2$, 2:1 hexane/ethyl acetate) to give 1,4-bis-[3-(3-carbomethoxymethylphenyl)-4-(2,3,4,6-tetra-O-acetyl-α-D-mannopyranosyloxy)phenyl]butane (0.88 g, 99%) as a foam. $^1$H NMR (400 MHz, $CDCl_3$): 7.38–7.44 (m, 6H), 7.25–7.29 (m, 2H), 7.17 (br s, 2H), 7.07–7.11 (m, 4H), 5.40 (s, 2H), 5.20–5.30 (m, 6H), 4.15 (dd, J=12.3, 4.8 Hz, 2H), 3.93 (dd, J=12.4, 2.2 Hz, 2H), 3.76–3.82 (m, 2H), 3.72 (s, 4H), 3.68 (s, 6H), 2.63 (m, 4H), 2.13 (s, 6H), 2.01 (s, 6H), 2.00 (s, 6H), 1.97 (s, 6H), 1.67 (m, 4H) ppm. IR(NaCl): 1748, 1219$cm^{-1}$.

Step 6

The per-acetate (0.87 g, 0.73 mmol) was dissolved in acetonitrile (3 mL) and treated with a solution of lithium hydroxide hydrate (0.46 g, 11 mmol in 2 mL water) and the mixture was stirred at room temperature overnight. The solvent was removed under reduced pressure and is the residue was acidified to pH 2 with concentrated hydrochloric acid. A portion of the mixture was purified by reverse-phase HPLC ($C_{18}$, water/acetonitrile gradient 20–80% over 45 minutes, monitored at 254 nm) to give 1,4-bis-[3-(3-carboxymethylphenyl)-4-(α-D-mannopyranosyloxy)

phenyl]butane (230 mg) as a white solid, m.p.: 195–197° C. $^1$H NMR(400 MHz, DMSO-d$_6$): 7.31–7.39(m,6H), 7.20–7.25(m, 4H), 7.10–7.15 (m, 4H), 5.25 (s, 2H), 4.88 (br d, J=4.0 Hz, 2H), 4.76 (br s, 2H), 4.60 (br s, 2H), 4.45 (br t, J=5.9 Hz, 2H), 3.55–3.68 (m, 5H), 3.62 (s, 4H), 3.40–3.50 (m, 7H), 2.60 (m, 4H), 1.62 (m, 4H) ppm. IR (KBr): 3333, 3229, 1729, 1224 cm$^{-1}$; Found: 61.30% C, 6.15% H: calc. for C$_{44}$H$_{50}$O$_{16}$.0.4 TFA: 61.32% C, 5.79% H.

EXAMPLE 4

N,N'-Bis-[4-(3-(3-carboxymethylphenyl)-4-(α-D-mannopyranosyloxy)phenylbutan-1-oyl]-4,4'-trimethylenedipiperidine Step 1

Succinic anhydride (2.0 g, 19.9 mmol) and aluminum chloride (17.7 g, 132 mmol) were mixed with 1,2-dichloroethane (45 mL) and cooled in an ice bath. The mixture was treated with a solution of 3-(2-(2,3,4,6-tetra-O-pivaloyl-α-D-mannopyranosyloxy)phenyl)phenylacetic acid ethyl ester (10.0 g, 13.2 mmol) in dichloroethane (10 mL) and the mixture was stirred overnight while the bath temperature gradually came to room temperature. The reaction was mixed with ice water (100 mL) and stirred for 15 minutes. The organic materials were isolated, and the aqueous portion was extracted with dichloromethane (3×5 mL). The organic materials were combined, dried (MgSO$_4$) then concentrated under reduced pressure, to give 12 (13.5 g) which was used without further purification. IR (NaCl): 1738, 1685, 1228 cm$^{-1}$.

Step 2

The acid (12)(13.5 g, 19.7 mmol) was dissolved in dichloromethane (65 mL), and treated with boron trifluoride etherate (15.3 mL, 122 mmol), then trifluoroacetic acid (9.4 mL, 122 mmol). The mixture was then treated with triethylsilane (9.4 mL, 59.1 mmol) and stirred at room temperature overnight. The reaction was mixed with water (200 mL) and the organic materials were separated. The aqueous portion was extracted with dichloromethane (3×10 mL) and the extracts were combined with the original organic portion, dried (MgSO$_4$), then concentrated under reduced pressure to give 4-(3-(3-carboethoxymethylphenyl)-4-(2,3,4,6-tetra-O-pivaloyl-α-D-mannopyranosyloxy)phenyl) butanoic acid (13)(1.49 g, 97%) as a clear oil. IR (NaCl): 1737, 1132cm$^{-1}$.

Step 3

The acid 13 (16.0 g, 23.8 mmol) was mixed with thionyl chloride (50 mL) and the mixture was stirred at room temperature for 36 hours, then concentrated under reduced pressure to give the acid chloride 14 (16.3 g, 99%) which was used without further purification. IR (NaCl): 2974, 1797, 1740, 1135 cm$^{-1}$.

Step 4

4,4'-Trimethylenedipiperidine (0.4 g, 1.9 mmol) in dichloromethane (5 mL) was added to a solution of acid chloride 14 (2.8 g, 3.26 mmol) in dichloromethane (5 mL) at 0° C. Triethylamine (0.61 mL, 4.4 mmol) and 4-dimethylaminopyridine (35 mg, 10 mol %) were added and the mixture was stirred at room temperature for 1 hour, then mixed with water (20 mL). The organic materials were washed with saturated sodium chloride (20 mL), dried (MgSO$_4$) and concentrated under reduced pressure. The residue was purified by flash chromatography (SiO$_2$, 2:1 ethyl acetate:hexane) to give the bis-amide 15 (1.1 g, 18%). $^1$H NMR (400 MHz, CDCl$_3$): 7.40–7.45 (m, 4H), 6.98–7.30 (m, 10 H), 5.25–5.42 (m, 6H), 4.09–4.19 (m, 4H), 3.50–3.96 (m, 8H), 2.62–2.69 (m, 4H), 2.28–2.36 (m, 4H), 1.90–2.02 (m, 4H), 1.60–1.74 (m, 6H), 1.35–1.50 (m, 2H), 1.24 (s, 18H), 1.15 (s, 18H), 1.11 (s, 36H), 1.08–1.28 (m, 26H). IR(NaCl): 1739 cm$^{-1}$.

Step 5

Bis-amide 15 (1.0 g, 0.54 mmol) was dissolved in THF (3 mL) and treated with aqueous sodium hydroxide (0.40 g, 10 mmol, in 3 mL water). The mixture was stirred at room temperature overnight. The THF was removed under reduced pressure and the residue was acidified to pH 2 with concentrated hydrochloric acid, and purified by reverse-phase HPLC to give N,N'-bis-[4-(3-(3-carboxymethylphenyl)-4-(α-D-mannopyranosyloxy)phenyl)butan-1-oyl]-4,4'-trimethylenedipiperidine (17)(30 mg, 5%) as a white solid, m.p.: 119–121° C. $^1$H NMR (400 MHz, DMSO-d$_6$): 7.32–7.40 (m, 6H), 7.20–7.27 (m, 4H), 7.10–7.14 (m, 4H), 5.26 (br s, 2H), 4.36 (br d, J=11 Hz, 2H), 4.05 (br s, 8H), 3.77 (br d, J=11 Hz, 2H), 3.50–3.70 (m, 8H), 3.40–3.52 (m, 5H), 3.31–3.40 (m, 2H), 2.92 (br t, J=14 Hz, 2H), 2.55–2.62 (m, 4H), 2.42–2.53 (m, 3H), 2.27–2.34 (m, 4H), 1.73–1.82 (m, 4H), 1.57–1.67 (m, 4H), 1.36–1.47 (m, 2H), 1.22–1.33 (m, 2H), 1.11–1.20 (m, 4H), 0.80–1.02 (m, 4H). IR (KBr): 3415, 1713, 1609 cm$^{-1}$. MS (FAB): 1150 (M$^+$+Na). Analysis: calculated for C$_{61}$H$_{78}$N$_2$O$_{18.1.4}$ TFA: 59.54% C, 6.22% H, 2.18% N. Found: 59.65% C, 6.56% H, 2.23% N.

EXAMPLE 5

Di-6-[3-(3-carboxymethylphenyl)-4-(2-α-D-mannopyranosyloxy)phenyl]hexylether

Step 1

Oxalyl chloride (1.65 mL, 2M in dichloromethane, 3.30 mmol) was added to anhydrous dichloromethane (10 mL) at −78° C. Dimethylsulfoxide (0.56 mL, 7.26 mmol) was added dropwise over several minutes and the resulting solution was stirred for 10 minutes. Ethyl 6-hydroxyhexanoate (0.50 mL, 3.07 mmol) was added dropwise, and after thirty minutes triethylamine (2.10 mL, 15.1 mmol) was added dropwise. The cooling bath was removed, and after 15 minutes water (10 mL) was added. The mixture was stirred for 10 minutes, the layers were separated and the aqueous layer was extracted with dichloromethane. The organic layers were combined and dried (MgSO$_4$), then the solvent was removed in vacuo. Silica gel chromatography (2:1 hexanes:ethyl acetate) afforded pure product (0.44 g, 91%). $^1$H NMR (400 MHz, CDCl$_3$): 9.75 (1H), 4.10 (2H), 2.45 (2H), 2.30 (2H), 1.65 (4H), 1.24 (3H).

Step 2

Triethylsilane (0.89 mL, 5.57 mmol) and triethylsilyl trifluoromethanesulfonate (63 mL, 0.28 mmol) were dissolved in anhydrous dichloromethane (6 mL) at 0° C. and a solution of 5-carboethoxypentanal (0.44 g, 2.78 mmol) in dichloromethane (3 mL) was added. The cooling bath was removed and the reaction was stirred at room temperature for 80 minutes. The solvent was removed in vacuo and the residue was purified by silica gel chromatography (6:1 hexanes:ethyl acetate) to yield the product (0.31 g, 74%). $^1$H NMR (400 MHz, CDCl$_3$): 4.10 (4H), 3.37 (4H), 2.28 (4H), 1.60 (8H), 1.36 (4H), 1.24 (6H).

Step 3

Di-5-carboethoxypentylether (0.16 g, 0.53 mmol) was dissolved in methanol (1 mL) and 1N sodium hydroxide solution (1.05 mL, 1.05 mmol) was added. The resulting solution was stirred at room temperature for 3 hours. Methanol was removed under reduced pressure and the remaining solution was acidified (conc. HCl) and extracted with two portions of diethyl ether. The extracts were combined, dried (MgSO$_4$), and concentrated under reduced pressure. The residue was reconcentrated twice from acetonitrile to give the product as a white solid (0.16 g, quantitative). $^1$H NMR (400 MHz, CDCl$_3$): 3.40 (4H), 2.36 (4H), 1.60 (8H), 1.42 (4H).

Step 4

Di-5-carboxypentylether (0.15 g, 0.53 mmol) and DMF (1 drop) were dissolved in anhydrous dichloromethane (2.5 mL) and the resulting solution was cooled to 0° C. Oxalyl chloride solution (0.59 mL of 2M in dichloromethane, 1.18 mmol) was added slowly. The reaction was stirred at 0° C. for 5 minutes, then the cooling bath was removed and stirring was continued for 20 minutes at room temperature. The solution was cooled to 0° C. and a solution of 3-(2-methoxyphenyl)phenylacetic acid ethyl ester (0.29 g, 1.07 mmol) in dichloromethane (1 mL) was added. Aluminum chloride was added in three portions (0.17 g, 0.17 g, 0.08 g, total 3.15 mmol) at one minute intervals. The solution was stirred for five minutes, then poured onto ice and extracted with two portions of ethyl acetate. The organic layers were combined and washed with water, saturated sodium bicarbonate solution, and saturated sodium chloride solution. The resulting solutici was dried (MgSO$_4$) and concentrated under reduced pressure. Silica gel chromatography (gradient of 4:1 to 1:1 hexanes:ethyl acetate) gave the product as a yellow oil (0.34 g, 85%). $^1$H NMR (400 MHz, CDCl$_3$): 7.91 (4H), 7.41 (6H), 7.28 (2H), 6.99 (2H), 4.14 (4H), 3.86 (6H), 3.66 (4H), 3.40 (4H), 2.94 (4H), 2.16 (4H), 1.75 (4H), 1.59 (4H), 1.43 (4H), 1.26 (6H).

Step 5

Di-6-[3-(3-carboethoxymethylphenyl)-4-methoxyphenyl]-6-oxohexylether (0.34 g, 0.45 mmol) was dissolved in anhydrous dichloromethane (2.5 mL) and the resulting solution was cooled to 0° C. Trifluoroacetic acid (0.23 mL, 3.0 mmol) was added, then triethylsilane (0.29 mL, 1.8 mmol) and boron trifluoride etherate (0.33 mL, 2.7 mmol). The cooling bath was removed and the reaction was stirred for 1 h at rt. Dichloromethane was added and the resulting mixture was extracted with saturated sodium bicarbonate solution and water. The organic layer was dried (MgSO$_4$) and concentrated under reduced pressure. Silica gel chromatography (6:1 hexane:ethyl acetate) gave the product as a clear oil (0.23 g, 71%). $^1$H NMR (400 MHz, CDCl$_3$): 7.42 (4H), 7.35 (2H), 7.25 (2H), 7.09 (4H), 6.87 (2H), 4.16 (4H), 3.77 (6H), 3.65 (4H), 3.37 (4H), 2.57 (4H), 1.57 (10H), 1.35 (8H), 1.25 (6H).

Step 6

Di-6-[3-(3-carboethoxymethylphenyl)-4-methoxyphenyl] hexylether (0.23 g, 0.32 mmol) was dissolved in dry dichloromethane (1.6 mL) and the solution was cooled to 0° C. Boron tribromide solution (1M in dichloromethane, 1.40 mL, 1.40 mmol) was added dropwise and the cooling bath was removed. After twenty minutes the solution was again cooled to 0° C. and absolute ethanol (1 mL) was added dropwise. The reaction mixture was then poured onto ice and extracted with ethyl acetate. The organic layer was washed with saturated sodium chloride solution and dried (MgSO$_4$), then concentrated under reduced pressure. Silica gel chromatography (2:1 to 1:1 hexanes:ethyl acetate) gave the product (0.11 g, 50%). $^1$H NMR (400 MHz, CDCl$_3$): 7.42 (8H), 7.04 (4H), 6.88 (2H), 5.14 (2H), 4.16 (4H), 3.67 (4H), 3.38 (4H), 2.57 (4H), 1.85 (4H), 1.62 (6H), 1.40 (6H), 1.27 (6H).

Step 7

2,3,4,6-Tetra-O-pivaloyl-α-D-mannopyranosyl fluoride (0.52 g, 1.00 mmol) and di-6-[3-(3-carboethoxymethylphenyl)-4-hydroxyphenyl]hexylether (0.23 g, 0.33 mmol) were dissolved in dry dichloromethane (2 mL) and the solution was cooled to 0° C. Boron trifluoride etherate (0.38 mL, 3.10 mnuol) was added slowly and the reaction was stirred for 90 minutes. The reaction mixture was diluted with ethyl acetate and washed with two portions of water, then 1N NaOH, water, and saturated sodium chloride solution. The resulting solution was dried (MgSO$_4$) and concentrated under reduced pressure. The residue was purified by silica gel chromatography (15:1 hexanes:ethyl acetate) to give the product (0.45 g, 82%). $^1$H NMR (400 MHz, CDCl$_3$): 7.45 (7H), 7.15 (7H), 5.32 (8H), 4.14 (4H), 3.86 (4H), 3.72 (4H), 3.54 (2H), 3.40 (4H), 2.59 (4H), 1.85 (4H), 1.62 (4H), 1.46 (4H), 1.36 (4H), 1.26 (24H), 1.15 (18H), 1.10 (36H).

Step 8

Di-6-[3-(3-carboethoxymethylphenyl)-4-(2,3,4,6-tetra-O-pivaloyl-α-D-mannopyranosyloxy)phenyl]hexylether (0.45 g, 0.27 mmol) was dissolved in anhydrous tetrahydrofuran (0.9 mL) and methanol (1.8 mL). Sodium methoxide (49 mg, 0.84 mmol) was added, and the reaction mixture was stirred at room temperature overnight. Another portion of sodium methoxide (50 mg, 0.93 mmol) was added, followed after four hours with a third portion (112 mg, 2.07 mmol). The reaction was continued for another four hours, then the mixture was filtered and the collected solid was washed with a 2:1 mixture of tetrahydrofuran and methanol. The solid was then dissolved in water (1 mL), and sodium hydroxide solution (1M) was added until the pH reached 14. This solution was stirred for four hours, then neutralized with pre-washed Dowex 50 ion exchange resin (H$^+$ form). The resin was filtered away and the filtrate was lyophilized. The product was then dried in vacuo over P$_2$O$_5$ to give di-6-[3-(3-carboethoxymethylphenyl)-4-(α-D-mannopyranosyloxy)phenyl]hexylether (0.21 g, 78%). $^1$H NMR (400 MHz, CD$_3$CN/D$_2$O): 7.46 (2H), 7.34 (2H), 7.16 (10H), 5.31 (2H), 3.79 (2H), 3.66 (2H), 3.57 (4H), 3.42 (5H), 3.28 (2H), 2.56 (4H), 1.80 (4H), 1.60 (4H), 1.36 (6H).

EXAMPLE 6

S,S-Bis-[3-(3-carboxymethylphenyl)-4-(α-D-mannopyranosyloxy)-3-phenylprop-1-yl]-1,3-dithiopropane Step 1

Part A: 3-(2-Methoxyphenyl)phenylacetic acid ethyl ester (5.04 g, 18.66 mmol) and 3-bromopropionyl chloride (1.88 mL, 18.66 mmol) were mixed with dichloroethane (30 mL). The mixture was cooled in an ice-water bath and treated with aluminum chloride (7.6 g, 57 mmol). After 15 minutes the reaction was mixed with ice-water (100 mL), and the organic materials were separated. The aqueous portion was extracted with dichloromethane (3×5 mL), and the organic materials were combined, dried (MgSO$_4$), concentrated under reduced pressure. The residue was used in the next step without further purification.

Part B: The product from part A (8.5 g, 19 mmol) was dissolved in dichloromethane (40 mL) and cooled in an ice-water bath. Trifluoroacetic acid (5.9 mL, 76 mmol), triethylsilane (6.1 mL, 38 mmol) then boron trifluoride etherate (9.4 mL, 76 mmol) were added and the cooling bath was removed. The mixture was stirred at room temperature overnight then cooled in an ice bath and quenched with cold water (100 mL). The organic materials were separated, and the aqueous portion was extracted with dichloromethane (3×10 mL), and the organic materials were combined, washed with saturated sodium chloride solution (50 mL), dried (MgSO$_4$) and concentrated under reduced pressure to provide 3-(2-methoxyphenyl-5-(3-bromopropyl)) phenylacetic acid ethyl ester (6.53 g, 90%) $^1$H NMR (400 MHz, CDCl$_3$): 7.41–7.45 (m, 2H), 7.36 (t, J=8 Hz, 1H), 7.25–7.28 (m, 1H), 7.12–7.16 (m, 2H), 6.90 (d, J=8.6 Hz, 1H), 4.15 (q, J=7.0 Hz, 2H), 3.78 (s, 3H), 3.67 (s, 2H), 3.41 (t, J=6.6 Hz, 2H), 2.75 (t, J=7.0 Hz, 2H), 2.15 (m, 2H), 1.26 (t, J=7.3 Hz, 3H), IR (NaCl): 1736 cm$^{-1}$.

Step 2

A solution of 1,3-propanedithiol (0.109 g, 0.94 mmol) in THF (4.5 mL) was degassed under nitrogen, and cooled in an ice-water bath. Sodium hydride (86.5 mg, 2.1 mmol) was added and the mixture was stirred at room temperature for 2 hours. A solution of the bromide from step 1 (0.83 g, 2.12 mmol) in THF (1.0 mL) was added and the mixture was stirred at reflux overnight. The reaction was partitioned between water and ethyl acetate (20 mL of a 1:1 mixture), and the organic materials were separated, washed with saturated sodium chloride (20 mL) and dried (MgSO$_4$), then concentrated under reduced pressure. The residue was purified by flash chromatography (SiO$_2$, gradient elution, hexane to 3:1 hexane/ethyl acetate) to give S,S-bis-[3-(3-carboethoxymethylphenyl)-4-(methoxy)-3-phenylprop-1-yl]-1,3-dithiopropane (166.2 mg, 24%). $^1$H NMR (400 MHz, CDCl$_3$): 7.39–7.45 (m, 4H), 7.32–7.38 (m, 2H), 7.21–7.28 (m, 2H), 7.08–7.15 (m, 4H), 6.85–6.92 (m, 2H), 4.14 (q, J=7.0 Hz, 4H), 3.77 (s, 6H), 3.65 (s, 4H), 2.80–2.95 (m, 2H), 2.77 (t, J=7.3 Hz, 2H), 2.68 (t, J=8.0 Hz, 4H), 2.60 (t, J=7.0 Hz, 2H), 2.52 (t, J=7.0 Hz, 2H), 2.04–2.16 (m, 2H), 1.81–1.93 (m, 4H), 1.25 (t, J=7.0 Hz, 6H). IR (NaCl): 1731 cm$^{-1}$.

Step 3

A solution of the bis-thioether from step 2 (70.7 mg, 0.1 mmol) in dichloromethane (2 mL) was cooled in a dry-ice/acetone bath and treated with boron tribromide (0.8 mL of a 1M solution in dichloromethane, 0.8 mmol) and the mixture stood at −10° C. overnight. The reaction was mixed with water (10 mL) and the mixture was extracted with dichloromethane (3×2 mL). The organic materials were combined, dried (MgSO$_4$) and concentrated under reduced pressure, to give S,S-bis-[3-(3-carboethoxymethylphenyl)-4-(hydroxy)-3-phenylprop-1-yl]-1,3-dithiopropane (68 mg, 100%). $^1$NMR (400 MHz, CDCl$_3$): 7.43 (t, J=7.7 Hz, 2H), 7.34–7.39 (m, 4H), 7.30 (br d, J=7.3 Hz, 2H), 7.03–7.08 (m, 4H), 6.87 (br d, J=8.8 Hz, 2H), 4.96–5.30 (br s, 2H), 4.15 (q, J=7.0 Hz, 4H), 3.66 (s, 4H), 2.66 (t, J=7.3 Hz, 4H), 2.60 (t, J=7.0 Hz, 2H), 2.52 (t, J=7.0 Hz, 4H), 1.80–1.92 (m, 6H), 1.26 (t, J=7.3 Hz, 6H), 1.21–1.27 (m, 2H). IR (NaCl): 3420, 1726 cm$^{-1}$.

Step 4

The phenol (0.47 g, 0.68 mmol) and α-D-mannose pentaacetate (0.8 g, 2.0 mmol) were mixed with dichloroethane (8 mL) and treated with borontrifluoride etherate (1.0 mL, 8.0 mmol). The reaction was stirred at room temperature overnight, then quenched with water (10 mL). The organic materials were separated, and the aqueous portion was extracted with dichloromethane (3×2 mL). The organic materials were combined, dried (MgSO$_4$) then concentrated under reduced pressure. The residue was purified by flash chromatography (SiO$_2$, gradient elution, 3:1 hexane/ethyl acetate to 1:1 hexane/ethyl acetate) to give S,S-bis-[3-(3-carboethoxymethylphenyl)-4-(2,3,4,6-tetra-O-acetyl-α-D-mannopyranosyloxy)-3-phenylprop-1-yl]-1,3-dithiopropane (0.331 g, 36%) IR (NaCl): 1752 cm$^{-1}$.

Step 5

The per-acetate (0.64 g, 0.47 mmol) was dissolved in acetonitrile (5 mL) and treated with a solution of sodium hydroxide (5.0 mL of a 2N solution, 10 mmol), then stirred at rt overnight. The mixture was acidified with concentrated hydrochloric acid to pH 2, and the volatiles were removed under reduced pressure. A portion of the aqueous residue was purified by reverse-phase chromatography to provide S,S-bis-[3-(3-carboxymethylphenyl)-4-(α-D-mannopyranosyloxy)-3-phenylprop-1-yl]-1,3-dithiopropane as a white solid, m.p.: 96–100° C. $^1$H NMR(400 MHz, DMSO-d$_6$): 7.31–7.39(m,6H), 7.20–7.27 (m, 4H), 7.11–7.15 (m, 4H), 5.26 (s, 2H), 3.30–3.75 (m, 28H), 2.64 (t, J=7.7 Hz, 4H), 2.57 (t, J=7.0 Hz, 4H), 2.45–2.52 (m, 4H), 1.75–1.84 (m, 4H), 1.66–1.74 (m, 2H). IR (KBr): 3430, 1711 cm$^{-1}$.

EXAMPLE 7

1,6-Bis-[3-(3-carboxymethylphenyl)-4-(α-D-mannopyranosyloxy)phenyl]-1,6-bis-cxohexane Step 1

3-(2-(2,3,4,6-Tetra-O-acetyl-α-D-nmannopyranosyloxy) phenyl)phenylacetic acid ethyl ester (0.56 g, 0.96 mmol) and adipoyl chloride (0.068 mL, 0.47 mmol) were dissolved in dichloroethane (5 mL) and cooled in an ice-water bath and treated with aluminum chloride (2.56 g, 19.2 mmol). After 1.5 h, the reaction was mixed with ice water (25 mL) and stirred for 15 minutes. The organic materials were isolated, and the aqueous portion was extracted with dichloromethane (3×2 mL). The organic materials were combined, dried (MgSO$_4$), then concentrated under reduced pressure. The residue was purified by flash chromatography (SiO$_2$, 1:1 hexane/ethyl acetate), to give 1,6-bis-[3-(3-carboethoxymethylphenyl)4-(2,3,4,6-tetra-O-acetyl-α-D-mannopyranosyloxy)phenyl]-1,6-bis-oxohexane (0.43 g, 35%). $^1$H NMR (400 MHz, CDCl$_3$): 8.00 (d, J=2.2 Hz, 2H), 7.93 (dd, J=8.6, 2.2 Hz, 2H), 7.42–7.48 (m, 6H), 7.31–7.35 (m, 2H), 7.25–7.29 (m, 2H), 5.60 (d, J=0.2 Hz, 2H), 5.31–5.34 (m, 2H), 5.28 (d, J=9.1 Hz, 2H), 5.23–5.28 (m, 2H), 4.21 (dd, J=12.3, 5.1 Hz, 2H), 4.15 (q, J=7.4 Hz, 4H), 3.98 (dd, J=12.4, 2.2 Hz, 2H), 3.79–3.85 (m, 2H), 3.73 (s, 4H), 3.00–3.06 (m, 4H), 2.17 (s, 6H), 2.03 (s, 6H), 2.01 (s, 6H), 1.98 (s, 6H), 1.81–1.85 (m, 4H), 1.26 (t, J=7.5 Hz, 6H). IR (NaCl): 1747, 1680 cm$^{-1}$.

Step 2

The per-acetate (0.43 g, 0.33 mmol) was dissolved in acetonitrile (4 mL) and the solution was stirred with 2N sodium hydroxide (1.8 mL, 3.6 mmol). After 18 h at rt, the reaction mixture was neutralized with Dowex 50W acid ion exchange resin, and the volatiles were removed under reduced pressure. A portion of the residue was purified by reverse-phase HPLC, to give 1,6-Bis-[3-(3-carboxymethylphenyl)-4-(α-D-mannopyranosyloxy) phenyl]-1,6-bis-oxohexane as a white solid, m.p.: 127–129° C. $^1$H NMR (400 MHz, DMSO-d$_6$): 7.98 (d, J=8.8 Hz, 2H), 7.90 (s, 2H), 7.35–7.48 (m, 8H), 7.27 (d, J=8.6 Hz, 2H), 5.53 (s, 2H), 3.71 (s, 2H), 3.66 (s, 4H), 3.60 (d, J=11.4 Hz, 2H), 3.42–3.51 (m, 6H), 3.28–3.35 (m, 2H), 3.07–3.15 (m, 4H), 1.67–1.73 (m, 4H). IR (KBr): 3430, 1716, 1672 cm$^{-1}$. Analysis: calculated for C$_{46}$H$_{50}$O$_{18}$.0.6 TFA: 59.10% C, 5.32% H. Found: 58.92% C, 5.68% H.

EXAMPLE 8

1,3,5-Tris-[3-(3-carboxymethylphenyl)-4-(2-α-D-mannopyranosyloxy)phenylmethyl]benzene Step 1

1,3,5-Benzenetricarbonyl trichloride (1.0 g, 3.8 mmol) was dissolved in 1,2-dichloroethane (20 mL). Aluminum chloride (2.6 g, 18.8 mmol) was added, then by 3-(2-methoxyphenyl)phenylacetic acid methyl ester (4.8 g, 18.8 mmol) and the mixture was heated at 65° C. overnight. After cooling in an ice bath, ice water (20 mL) was added slowly. The organic materials were isolated, and the aqueous portion was extracted with methylene chloride (3×5 mL). The organic materials were combined, dried (MgSO$_4$) and concentrated under reduced pressure. The residue was purified by flash chromatography (SiO$_2$, gradient elution from hexane to 1:1/hexane:ethyl acetate) to give the triketone 33(f= 1), (1.05 g, 30%) $^1$H NMR (400 MHz, CDCl$_3$): 8.38 (d, J=1.5 Hz, 3H), 7.93 (m, 3H), 7.80–7.83 (m, 3H), 7.45 (m, 6H), 7.38 (t, J=7.3 Hz, 3H), 7.21–7.29 (m, 3H), 6.95 (dd, J=8.76, 1.44 Hz, 3H), 3.88 (s, 9H), 3.67 (s, 6H), 3.66 (s, 9H) ppm. IR (NaCl): 1734, 1654 cm$^{-1}$.

Step 2

The triketone 33 (3.13 g, 3.4 mmol) was dissolved in dichloromethane (16 mL), cooled in an ice bath, and treated with triethylsilane (3.8 mL, 23.7 mmol), trifluoroacetic acid (2.6 mL, 33.8 mmol), and boron trifluoride diethyl etherate (4.3 mL, 33.8 mmol). The mixture was stirred at room temperature for 1 h, then mixed with water (25 mL). The organic materials were isolated, and the aqueous portion was extracted with methylene chloride (3×5 mL). The organic materials were combined, dried (MgSO$_4$) then concentrated under reduced pressure. The residue was flushed through silica gel with hexane:ethyl acetate/3:1, and concentrated to provide 1,3,5-tris-[3-(3-carbomethoxymethylphenyl)-4-(2-methoxy)phenylmethyl]benzene (0.88 g, 28%). $^1$H NMR (400 MHz, CDCl$_3$): 7.38–7.43 (m, 6H), 7.33 (t, J=7.68 Hz, 3H), 7.23 (s, 3H), 7.14 (d, J=2.2 Hz, 3H), 7.08 (dd, J=8.08, 1.84 Hz, 3H), 6.90 (s, 3H), 6.85 (d, J=8.4 Hz, 3H), 3.89 (s, 6H), 3.76 (s, 9H), 3.68 (s, 9H), 3.66 (s, 6H) ppm. IR (NaCl): 1738 cm$^{-1}$.

Step 3

Part A: 1,3,5-Tris-[3-(3-carbomethoxymethylphenyl)-4-(2-methoxy)phenylmethyl]benzene (0.88 g, 1.0 mmol) was dissolved in dichloromethane (5 mL), and chilled in a dry ice/acetone bath. Boron tribromide (0.7 mL, 7.0 mmol) was added slowly, and the mixture was stirred at 0° C. for 2 h, then mixed with ice-water (10 mL). The organic materials were isolated, and the aqueous portion extracted with methylene chloride (3×5 mL). The organic materials were combined, dried (MgSO$_4$) then concentrated under reduced pressure to give 0.82 g of the crude product.

Part B: The residue from part A was mixed with methanol (20 mL) and sulfiric acid (1 mL) was added. The mixture was heated at reflux overnight, then concentrated under reduced pressure. The residue was mixed with dichloromethane (20 mL) and saturated sodium bicarbonate solution (10 mL). The organic phase was separated, dried (MgSO$_4$), and concentrated under reduced pressure. The residue was flushed through silica gel with hexane:ethyl acetate/1:1, and concentrated to provide 1,3,5-tris-[3-(3-carbomethoxymethylphenyl)-4-(2-hydroxy)phenylmethyl] benzene (0.63 g, 75%). $^1$H NMR (400 MHz, CDCl$_3$): 7.20–7.50 (m, 12H), 7.0 (d, J=2.2 Hz, 2H), 6.98 (s, 2H), 6.95 (dd, J=8.08, 2.2 Hz, 2H), 6.83 (s, 3H), 6.77 (d, J=8.44, 3H), 3.85 (s, 6H), 3.69 (s, 9H), 3.66 (s, 6H) ppm. IR (NaCl): 3429, 1737 cm$^{-1}$.

Step 4

The triphenol (0.62 g, 0.7 mmol) was dissolved in 1,2-dichloroethane (4 mL), α-D-mannose pentaacetate (1.4 g, 3.7 mmol) was added, followed by slow addition of boron trifluoride etherate (1.6 mL, 13.3 mmol). The mixture was stirred overnight at rt, then mixed with water (10 mL). The organic material was separated, and the aqueous portion was extracted with dichloromethane (3×2 mL). The organic fractions were combined, dried (MgSO$_4$), then concentrated under reduced pressure. The residue was purified by flash chromatography (SiO$_2$, gradient elution, hexane to 2:1/ethyl acetate:hexane) to provide 1,3,5-tris-[3-(3-carbomethoxymethylphenyl)-4-(2-(2,3,4,6-tetra-O-acetyl)-α-D-mannopyranosyloxy)phenylmethyl]benzene (0.9 g, 67%). $^1$H NMR (400 MHz, CDCl$_3$): 6.98–7.50 (m, 21H), 6.86 (s, 3H), 5.26 (m, 3H), 3.90–3.93 (m, 6H), 3.89 (s, 6H), 3.71 (s, 6H), 3.66 (s, 9H), 1.94–2.13 (m, 36H) ppm. IR (NaCl): 1745 cm$^{-1}$.

Step 5

The per-acetate (0.88 g, 0.48 mmol) was dissolved in acetonitrile (2 mL), and treated with lithium hydroxide monohydrate (0.4 g, 9.6 mmol) in water (2 mL). The mixture was stirred at rt overnight, then acidified to pH 2 with concetrated hydrochloric acid. The mixture was concentrated under reduced pressure, and the residue purified by HPLC (C-18 reverse-phase, gradient elution 20–80% acetonitrile in water, monitored at 254 nm) to give 1,3,5-tris-[3-(3-carboxymethylphenyl)-4-(2-α-D-mannopyranosyloxy) phenylmethyl]benzene (0.35 g, 57%) as a white solid, m.p. 155–158° C. $^1$H NMR (400 MHz, DMSO-d$_6$): 7.27–7.34 (m, 9H), 7.17–7.22 (m, 9H), 7.08–7.10 (dd, J=8.44, 1.70 Hz, 3H), 7.01 (s, 3H), 5.24 (s, 3H), 3.85 (s, 6H), 3.33–3.64 (m, 24H) ppm. IR (KBr): 3431, 1710 cm$^{-1}$. Anal.: calc. for C$_{69}$H$_{72}$O$_{24}$.1.0 TFA: 60.94%C, 5.26%H. Found: 60.85%C, 5.23%H.

EXAMPLE 9

1,3,5-Tris-[4-[3-(3-carboxymethylphenyl)-4-(α-D-mannopyranosyloxy)phenyl]-4-oxo-2-thiobutyl]

benzene

Step 1

3-(2-(2,3,4,6-Tetra-O-acetyl-α-D-mannopyranosyloxy) phenyl)phenylacetic acid ethyl (0.32 g, 0.547 mmol) and bromoacetyl bromide (0.06 mL, 0.689 mmol) were dissolved in dichloroethane (3 mL) and cooled in a dry-ice/acetone bath. The mixture was treated with aluminum chloride (1.45 g, 10.9 mmol) and the bath was replaced with an ice-water bath. After 15 minutes, the reaction was mixed with ice water (25 mL) and stirred for 15 minutes. The organic materials were isolated, and the aqueous portion was extracted with dichloromethane (3×2 mL). The organic materials were combined, dried (MgSO$_4$) then concentrated under reduced pressure to give 0.387 g of the product which was used without further purification. $^1$NMR (400 MHz, CDCl$_3$): 8.03 (d, J=2.5 Hz, 1H), 7.95 (dd, J=8.8, 2.5 Hz, 1H), 7.41–7.47 (m, 3H), 7.35 (m, 1H), 7.31 (d,J=8.8 Hz, 1H), 5.62 (d, J=1.8 Hz, 1H), 5.21–5.34 (m, 3H), 4.42 (s, 2H), 4.10–4.25 (m, 5H), 3.99 (dd, J=12.1, 2.2 Hz, 1H), 3.80–3.85 (m, 1H), 3.74 (s, 2H), 2.18 (s, 3H), 2.03 (s, 3H), 2.02 (s, 3H), 1.98 (s, 3H), 1.26 (t, J=8.0 Hz, 3H). IR (NaCl): 1746, 1220 cm$^{-1}$.

Step 2

1,3,5-Tris-(mercaptomethyl)benzene (102 mg, 0.47 mmol) in THF (1 mL) was treated with sodium hydride (59.8 mg, 1.49 mmol) and the mixture was stirred at room temperature for 30 minutes. A solution of the α-bromoketone from step 1 (1.02 g, 1.44 mmol) in THF (2.0 mL) was added and the mixture was stirred at room temperature overnight. The reaction was mixed with water (10 mL), and extracted with ethyl acetate (3×5 mL). The organic materials were combined, dried (MgSO$_4$), and concentrated under reduced pressure. The residue was purified by flash chromatography (SiO$_2$, gradient elution, 3:1 hexane/ethyl acetate to 1:1 hexane/ethyl acetate) to give 1,3,5-tris-[4-[3-(3-carboethoxymethylphenyl)4-(2,3,4,6-tetra-O-acetyl-α-D-mannopyranosyloxy)phenyl]-4-oxo-2-thiobutyl]benzene (0.59 g, 60%). $^1$NMR (400 MHz, CDCl$_3$): 7.98 (d, J=2.5 Hz, 3H), 7.89 (dd, J=8.8, 2.5 Hz, 3H), 7.40–7.46 (m, 6H), 7.25–7.35 (m, 12H), 5.61 (s, 3H), 5.22–5.33 (m, 9H), 4.10–4.25 (m, 10H), 3.97 (dd, J=12.1, 2.2 Hz, 3H), 3.78–3.84 (m, 3H), 3.72 (s, 6H), 3.69 (s, 3H), 3.64 (s, 3H), 2.16 (s, 9H), 2.02 (s, 9H), 2.01 (s, 9H), 1.97 (s, 9H), 1.25 (t, J=8.0 Hz, 9H); IR (NaCl): 1747, 1219 cm$^{-1}$.

Step 3

The triester per-acetate from step 2 (0.59 g, 0.28 mmol) in THF (3 mL) was treated with a solution of freshly prepared sodium methoxide (93 mg, 4.04 mmol in 3 mL methanol) and the mixture was stirred at room temperature overnight. The precipitate which had formed was collected by vacuum filtration and washed several times with 2:1 THF/methanol, and dried under vacuum to give 0.38 g of a white solid. The solid was dissolved in water (12 mL), 2N sodium hydroxide was added to pH 14, and the mixture was stirred at rt for 4 h. The reaction was acidified with Dowex 50W acidic ion-exchange resin, filtered, and the volatiles were removed under reduced pressure. A portion of the aqueous residue was purified by reverse-phase chromatography to give 1,3,5-tris-[4-[3-(3-carboxymethylphenyl)-4-(α-D-mannopyranosyloxy)phenyl]-4-oxo-2-thiobutyl]benzene as a white solid, m.p.: 140–143° C. $^1$H NMR (400 MHz, DMSO-d$_6$): 7.95 (dd, J=8.8, 2.5 Hz, 3H), 7.89 (d, J=2.2 Hz, 3H), 7.32–7.45 (m, 12H), 7.26 (d, J=7.3 Hz, 3H), 7.16–7.20 (m, 3H), 5.54 (s, 3H), 5.05 (br s, 3H), 4.85 (br s, 3H), 4.70 (br s, 3H), 4.50 (br s, 3H), 3.88–3.92 (m, 6H), 3.58–3.73 (m, 18H), 3.40–3.49 (m, 6H), 3.30–3.40 (m, 6H plus H$_2$O). IR (KBr): 3429, 1708, 1669 cm$^{-1}$. Analysis: calculated for C$_{75}$H$_{78}$O$_{27}$S$_3$·1.8 TFA: 55.12% C, 4.79% H. Found: 55.14% C, 5.20% H.

EXAMPLE 10

Binding Assays

Compounds were assayed for their ability to inhibit the binding of E-, P-, and/or L-selectin to sialyl-Lewis$^x$.

The E-selectin binding assays involved assessing the ability of HL60 cells that express sialyl-Lewis$^x$ and Lewis$^x$ to purified E-selectin, P-selectin and L-selectin recombinant proteins (cell-protein assay). A similar binding assay utilizing purified glycolipids and purified L-selectin recombinant protein (glycolipid-protein) was used to assess L-selectin binding.

Cell-Protein Assay

E-selectin, P-selectin, and L-selectin were expressed in recombinant soluble form as fusion proteins possessing the amino terminal lectin, EGF, and complement regulatory-like repeats (CR) 1 and 2 fused to the hinge and constant heavy chain regions 1 and 2 of the mouse IgG$_{2A}$ cDNA. All selectin fusion cassettes were generated by PCR from the E-selectin cDNA purchased from R&D Systems (Minneapolis, Minn.), and from the P-selectin and L-selectin cDNAs that were PCR cloned from total RNA extracted from human placenta. The mouse IgG cDNA was cloned from PCR amplified cDNA generated from RNA extracted from the hybridoma cell line 402C10. All fusion cassettes were expressed from baculovirus vectors using the BakPAK method and SF21 cells purchased from Clonetech.

Recombinant fusion proteins were purified from baculovirus infected culture supernatants by immunoprecipitation using Dynal™ goat anti-mouse IgG coated magnetic beads. Mock beads were generated from uninfected SF21 culture supernatants. Following immunoprecipitation, beads incubated with mock culture supernatants did not bind HL60 cells that express sialyl-Lewis$^x$ served as a negative control. Beads incubated from E-, L- or P-selectin culture supernatants did bind HL60 cells.

HL60 cells (10$^7$ cells) were fluorescently labeled with calcein AMC-3099 (Molecular Probes) in RPMI 1640 with 10% fetal calf serum (FCS). The magnetic beads (7 μl, 4×10$^6$ beads/ml) were incubated in duplicate wells of a flexible 96 well microtiter plate along with 7 μl of compound at various concentrations and 7 μl of calcein-labeled HL60 cells. The plates were incubated for ten minutes at room temperature. The plate was then placed on a magnetic separator and incubated for 2 more minutes. While the assay plate remained on the separator, unbound HL60 cells were removed and the wells were washed twice with phosphate buffered saline (PBS) to remove any remaining unbound cells. The HL60 cells remaining bound to the beads were inspected by microscopy and then lysed by adding 50 ml of a 1% solution of NP40 in PBS. Binding was quantitated fluorimetrically using a Millipore Cytofluor 2350 fluorimeter. Dose response curves and the concentration of compound at which 50% of the cell binding was inhibited (IC$_{50}$) was determined.

The compounds referred to in the following Table are those compounds referred to as the particularly preferred compounds herein.

The results of these assays are set forth in the following Table:

| Table of in Vitro Selectin Assay Data | | | | |
|---|---|---|---|---|
| Compound | n = or m/p subst | E-Selectin IC$_{50}$ (mM) or % inhib. / (mM) | P-Selectin IC$_{50}$ (mM) or % inhib. / (mM) | L-Selectin IC$_{50}$ (mM) or % inhib. / (mM) |
| A-4 | 4 | 5.0 | 2.5 | 2.0 |
| A-5 | 5 | 0.4 | 0.3 | 0.3 |
| A-6 | 6 | 0.5 | 0.07 | 0.56 |
| A-7 | 7 | 0.5 | 0.4 | 0.75 |
| A-9 | 9 | 1.0 | 1.0 | 1.0 |
| B-m | m | 0/1 | 0.22 | 3.0 |
| B-p | p | 2.0 | 2.0 | 3.0 |
| C | | 2.5 | 0.7 | 0/2 |
| D | | 29/2 | 0.5 | 5.0 |
| E | 6 | 3.27 | 0.54 | 1.4 |
| F | 4 | 1.0 | 1.0 | 3.0 |
| G | | 1.5 | 1.0 | 0/3 |
| H | | 0.7 | 0.2 | 0.5 |
| J | | 4.0 | 0/3 | 2.0 |

That which is claimed is:

1. A compound of the formula:

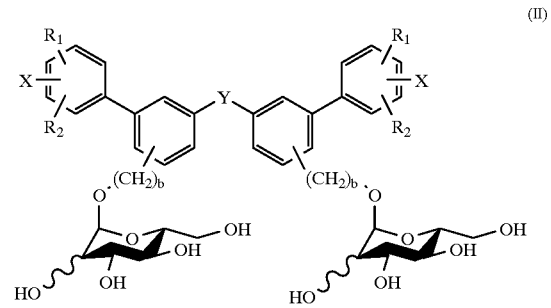

(II)

wherein X is selected from the group consisting of —CN, —(CH$_2$)$_n$CO$_2$H, —(CH$_2$)$_n$CONHOH, —O(CH$_2$)$_m$CO$_2$H, —O(CH$_2$)$_m$CONHOH, —(CH$_2$)$_n$CONHNH$_2$, —(CH$_2$)$_n$COZ, —(CH$_2$)$_n$Z, —CH(CO$_2$H)(CH$_2$)$_m$CO$_2$H, —(CH$_2$)$_n$O(CH$_2$)$_m$CO$_2$H, —CONH(CH$_2$)$_m$CO$_2$H, —CH(OZ)(CO$_2$H), —CH(Z)(CO$_2$H), —(CH$_2$)$_n$SO$_3$H, —(CH$_2$)$_n$PO$_3$D$_1$D$_2$, —NH(CH$_2$)$_m$CO$_2$H, —CONH(CHR$_3$)CO$_2$H, (1-H-tetrazolyl-5-alkyl-), and —OH;

For divalent structures, Y is —(CH$_2$)$_f$—, —CO(CH$_2$)$_f$CO—, —(CH$_2$)$_f$O(CH$_2$)$_f$—, —CO(CH$_2$)$_f$O $-(CH_2)_fCO-$, $-(CH_2)_gS(O)_b(CH_2)_fS(O)_b(CH_2)_g-$, $-CO(CH_2)_gS(O)_b(CH_2)_fS(O)_b(CH_2)_gCO-$, $-(CH_2)_fV(CH_2)_f-$, $-(CH_2)_fCOVCO(CH_2)_f-$, $-CO(CH_2)_fOVCO(CH_2)_fO-$, $-CO(CH_2)_fV(CH_2)_fCO-$, $-CONH(CH_2)_fNHCO-$, $-CO(CH_2)_fW(CH_2)_fCO-$, $-(CH_2)_fWSW(CH_2)_f-$, $-(CH_2)_fCONH(CH_2)_f NHCO(CH_2)_f-$, $-(CH_2)_fCOW(CH_2)_fWCO(CH_2)_f-$, or $-CH_2(CH_2)_fW(CH_2)_fCH_2-$ where V is $-N[(CH_2)_q]_2N-$ and q is independently 2 to 4, and W is aryl or heteroaryl;

For trivalent structures, Y is:

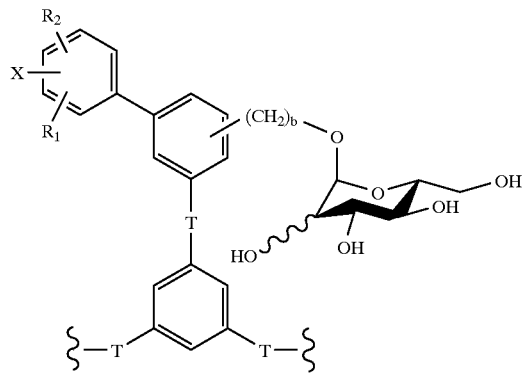

and T is selected from the group consisting of $-(CH_2)_f-$, $-CO(CH_2)_f-$, $-(CH_2)_gS(O)_b(CH_2)_f-$, and $-CO(CH_2)_gS(O)_b(CH_2)_f$, where the carbonyl group is positioned contiguous to the biphenyl unit;

$R_1$ and $R_2$ are independently selected from the group consisting of hydrogen, alkyl, halogen, $-OZ$, $-NO_2$, $-(CH_2)_nCO_2H$, $-NH_2$ and $-NHZ$;

$R_3$ is selected from the group consisting of hydrogen, alkyl, aralkyl, hydroxyalkyl, aminoalkyl, alkyl carboxylic acid and alkyl carboxamide;

f is 1 to 16, g is 0 to 6, n is 0 to 6, m is 1 to 6, p is 0 to 6, b is 0 to 2, Z is alkyl, aryl or aralkyl, and $D_1$ and $D_2$ are independently hydrogen or alkyl, and the pharmaceutically acceptable salts, esters, amides and prodrugs thereof.

2. A compound of the formula:

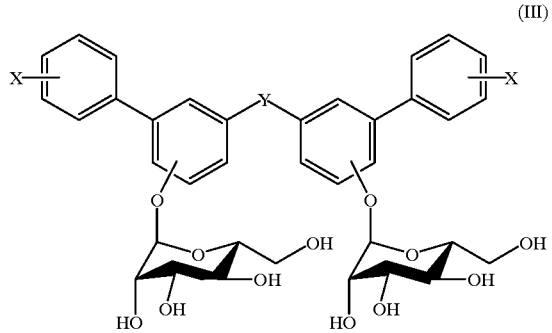

(III)

where X is $-COOH$, $-(CH_2)_nCOOH$ or $-O(CH_2)_nCOOH$ and Y is $-(CH_2)_n-$, $-(CH_2)_nW(CH_2)_n-$, $-(CH_2)_nWOW(CH_2)_n-$, $-(CH_2)_nS(CH_2)_nS(CH_2)_n-$, $-CO(CH_2)_nCO-$, or $-(CH_2)_nCOW(CH_2)_nWCO(CH_2)_n-$ where W is aryl or heteroaryl, and n is 0 to 6, and the pharmaceutically acceptable salts, esters, amides and prodrugs thereof.

3. A compound of claim 2 where Y is $-(CH_2)_f-$ or $-CH_2(CH_2)_fW(CH_2)_fH_2-$.

4. A compound of claim 2 where X is 3—$CH_2CO_2H$ and Y is $-(CH_2)_f-$ or $-CH_2(CH_2)_fW(CH_2)_fCH_2$.

5. A compound selected from:

1,7-bis-[3-(3-carboxymethylphenyl)-4-(2-α-D-mannopyranosyloxy)phenyl]heptane, 1,6-bis-[3-(3-carboxymethylphenyl)-4-(2-α-D-mannopyranosyloxy)phenyl]hexane, 1,5-bis-[3-(3-carboxymethylphenyl)-4-(2-α-D-mannopyranosyloxy)phenyl]pentane, 1,4-bis-[3-(3-carboxymethylphenyl)-4-(2-α-D-mannopyranosyloxy)phenyl]butane, N,N'-bis-[4-(3-(3-carboxymethylphenyl)-4-(α-D-mannopyranosyloxy)phenyl)$_{butan}$-1-oyl]-4,4'-trimethylenedipiperidine, S,S'-bis-[3-(3-carboxymethylphenyl)-4-(2-α-D-mannopyranosyloxy)-3-phenylprop-1-yl]-1,3-dithiopropane, 1,7-bis-[3-(3-carboxymethylphenyl)-4-(2-α-D-mannopyranosyloxy)phenyl]-1,7-bis-oxoheptane, 1,6-bis-[3-(3-carboxymethylphenyl)-4-(2-α-D-mannopyranosyloxy)phenyl]-1,6-bis-oxohexane, 1,5-bis-[3-(3-carboxymethylphenyl)-4-(2-α-D-mannopyranosyloxy)phenyl]-1,5-bis-oxopentane, 1,4-bis-[3-(3-carboxymethylphenyl)-4-(2-α-D-mannopyranosyloxy)phenyl]-1,4-bis-oxobutane, 1,3,5-tris-[3-(3-carboxymethylphenyl)4-(2-α-D-mannopyranosyloxy)phenylmethyl]benzene, and 1,3,5-tris-[4-[3-(3-carboxymethylphenyl)-4-(α-D-mannopyranosyloxy)phenyl]-4-oxo-2-thiobutyl]benzene.

6. 1,6-Bis-[3-(3-carboxymethylphenyl)-4-(2-α-D-mannopyranosyloxy)phenyl]hexane.

7. A pharmaceutical composition comprising a compound as in claim 1 and a pharmaceutically acceptable carrier.

8. A method of inhibiting the binding of E-selectin, P-selectin or L-selectin to $sLe^x$ or $sLe^a$ comprising administering to a patient an effective amount of a compound of claim 1.

9. A method of inhibiting the binding of E-selectin, P-selectin or L-selectin to $sLe^x$ or $sLe^a$ comprising administering to a patient an effective amount of 1,6-bis-[3-(3-carboxymethylphenyl)-4-(2-α-D-mannopyranosyloxy)phenyl]hexane.

* * * * *